US006221875B1

United States Patent
Darrow et al.

(12) 
(10) Patent No.: US 6,221,875 B1
(45) Date of Patent: Apr. 24, 2001

(54) SUBSTITUTED 9H-PYRIDINO [2,3-B]INDOLE AND 9H-PYRIMIDINO [4,5-B]INDOLE DERIVATIVES: SELECTIVE NEUROPEPTIDE Y RECEPTOR LIGANDS

(75) Inventors: James W. Darrow, Wallingford; George D. Maynard, Clinton; Raymond F. Horvath, North Branford; Jennifer Tran, Branford; Stephane De Lombaert, Madison, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/283,534

(22) Filed: Apr. 1, 1999

Related U.S. Application Data

(60) Provisional application No. 60/080,423, filed on Apr. 2, 1998.

(51) Int. Cl.[7] .............. A61K 31/437; A61K 31/496; A61K 31/497; A61K 31/5375; A61P 9/12
(52) U.S. Cl. ............ 514/292; 546/87; 544/106; 544/362; 544/405; 514/231.5; 514/252.13
(58) Field of Search ............... 546/87; 514/292, 514/231.5, 252.13; 544/106, 362, 405

(56) References Cited

U.S. PATENT DOCUMENTS

| 4,605,642 | 8/1986 | Rivier et al. ................... 424/177 |
| 5,063,245 | 11/1991 | Abreu et al. ................... 548/365 |
| 5,644,057 | 7/1997 | Yuan et al. ................... 544/280 |
| 5,955,613 * | 9/1999 | Horvath ................... 544/280 |

FOREIGN PATENT DOCUMENTS

| 0 061 056 | 3/1982 | (EP) . |
| 0 617 035 | 9/1994 | (EP) . |
| 94/13676 | 6/1994 | (WO) . |
| 96/33750 | 12/1995 | (WO) . |
| 96/35689 | 11/1996 | (WO) . |
| WO 97/20822 | 6/1997 | (WO) . |
| WO 98/29297 | 7/1998 | (WO) . |
| WO 98/45295 | 10/1998 | (WO) . |

OTHER PUBLICATIONS

Owens et al., "Physiology and Pharmacology of Corticotropin–releasing Factor," *Pharmacological Reviews*, vol. 43, pp. 425–473 (1972).

Volovenko et al., "Reaction of 4,5–Dihalopyrimidines with 2–Tosylmethylazahetarenes–One–Step Method for Obtaining Condensed Polynuclear Systems", *Khimiya Geterotsiklicheskikh Soedinelli*, pp. 852 (1991).

Posselt, "Die Einwirkung von Sauren auf Dianisyl–pyridyl–und Dipyridyl–anisyl–methanole", *Arzneim–Forsch*, pp. 1056–1065 (1978).

Eiden, et al., "Tetrahydrobenzodipyrandone und Tetrahydrobenzodipyrane", *Archiv der Pharmazie*, pp. 596–600 (1976).

* cited by examiner

Primary Examiner—Mukund J. Shah
Assistant Examiner—Venkataraman Balasubramanian
(74) Attorney, Agent, or Firm—Steven J. Sarussi; McDonnell Boehnen Hulbert & Berghoff

(57) ABSTRACT

Disclosed are compounds of the formula:

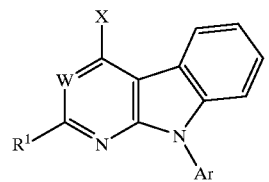

wherein Ar, $R^1$, W and X are substituents as defined herein, which compounds are effective neuropeptide Y1 receptor antagonists, and are therefore useful in the treatment of a wide variety of clinical conditions which are characterized by the presence of an excess of neuropeptide Y.

34 Claims, No Drawings

SUBSTITUTED 9H-PYRIDINO [2,3-B]INDOLE AND 9H-PYRIMIDINO [4,5-B]INDOLE DERIVATIVES: SELECTIVE NEUROPEPTIDE Y RECEPTOR LIGANDS

This application claims benefit from provisional application Ser. No. 60/080,423 filed Apr. 2, 1999.

BACKGROUND OF THE INVENTION

1. Field of the Invention

This invention relates to certain substituted 9H-pyridino [2,3-b]indole and 9H-pyrimidino[4,5-b]indole derivatives which selectively bind mammalian neuropeptide Y (NPY) receptors. This invention also relates to pharmaceutical compositions comprising such compounds. It further relates to the use of such compounds in treating physiological disorders associated with an excess of neuropeptide Y, especially feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of neuropeptide $NPY_1$ receptors is related to vasoconstriction, Wahlestedt et al., Regul. Peptides, 13: 307–318 (1986), McCauley and Westfall, J. Pharmacol. Exp. Ther. 261: 863–868 (1992), and Grundemar et al., Br. J. Pharmacol. 105: 45–50 (1992); and to stimulation of consummatory behavior, Flood and Morley, Peptides, 10: 963–966 (1989), Leibowitz and Alexander, Peptides, 12: 1251–1260 (1991), and Stanley et al., Peptides, 13: 581–587 (1992).

Grundemar and Hakanson, TiPS, May 1994 [Vol. 15], 153–159, state that, in animals, neuropeptide Y is a powerful stimuli of food intake, and an inducer of vasoconstriction leading to hypertension. They further point out that low levels of neuropeptide Y is associated with loss of appetite. These reports clearly indicate that compounds that inhibit the activity of this protein will reduce hypertension and appetite in animals.

SUMMARY OF THE INVENTION

Compounds that interact with $NPY_1$ receptors and inhibit the activity of neuropeptide Y at those receptors are useful in treating physiological disorders associated with an excess of neuropeptide Y, including eating disorders, such as, for example, obesity and bulimia, and certain cardiovascular diseases, for example, hypertension.

This invention provides novel compounds of Formula I which selectively bind to neuropeptide Y (NPY) receptors. Such compounds are useful in treating feeding disorders such as obesity and bulimia as well as certain cardiovascular diseases such as essential hypertension.

The novel compounds encompassed by the instant invention have general Formula I:

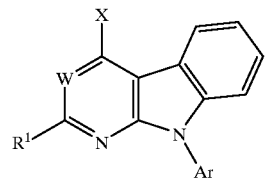

I wherein:

Ar is phenyl, 1- or 2-naphthyl, 2-, 3-, or 4-pyridyl, 2-, 4-or 5-pyrimidinyl, each of which is optionally mono-, di-, or trisubstituted with halogen, trifluoromethyl, hydroxy, amino, $C_1$–$C_6$ alkylamino, $C_1$–$C_6$ dialkylamino, $C_3$–$C_7$ cycloalkylamino, carboxamido, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, $C_3$–$C_7$ cycloalkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, ($C_3$–$C_7$ cycloalkyl) $C_1$–$C_6$ alkyl, $C_3$–$C_7$ cycloalkyl, or ($C_1$–$C_6$ alkylene)—$G^1$—$R^2$ wherein $G^1$ is oxygen or sulfur and $R^2$ is hydrogen, $C_1$–$C_6$ alkyl, or $C_3$–$C_7$ cycloalkyl;

W is N or C-$R^3$, wherein $R^3$ is hydrogen or $C_1$–$C_6$ alkyl;

X is

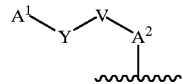

wherein $A^1$ is $NR^4R^5$ wherein $R^4$ and $R^5$ are independently hydrogen, a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;

$C_1$–$C_6$ alkanoyl, ($C_3$–$C_7$ cycloalkyl) $C_1$–$C_6$ alkanoyl, $C_3$–$C_7$ cycloalkanoyl, $C_1$–$C_6$ alkylsulfonyl, or $C_3$–$C_7$ cycloalkylsulfonyl with the proviso that $R^4$ and $R^5$ may not both be alkanoyl or alkylsulfonyl;

$C_1$–$C_6$ heterocycloalkyl, wherein heterocycloalkyl is morpholinyl, piperazinyl, piperidinyl, or pyrrolidinyl;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, $C_1$–$C_6$ dialkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where any 2 adjacent substituents may together form a 5-7 fused cycloalkyl or heterocycloalkyl ring;

$NR^4R^5$ taken together form a $C_3$–$C_6$ heterocycloalkyl, or a group of the formula:

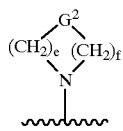

wherein e and f are independently 1, 2, or 3 and the sum of e and f is at least 3; and $G^2$ is
(i) $NR^6$ wherein $R^6$ is hydrogen, $C_1$–$C_6$ alkyl, ($C_3$–$C_7$ cycloalkyl) $C_1$–$C_6$ alkyl, or $C_3$–$C_7$ cycloalkyl; or
(ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—, —NH($C_3$–$C_7$ cycloalkyl)—, where $R^7$ is hydrogen, $C_1$–$C_6$ alkyl, ($C_3$–$C_7$ cycloalkyl) $C_1$–$C_6$ alkyl, or $C_3$–$C_7$ cycloalkyl; or
(iii) —$CONH_2$—, or —CO[N($C_1$–$C_6$ alkylene)$R^8$]— wherein $R^8$ is hydrogen, $C_1$–$C_6$ alkyl, ($C_3$–$C_7$ cycloalkyl) $C_1$–$C_6$ alkyl, or $C_3$–$C_7$ cycloalkyl;

$A^2$ is NH, $SO_2$, oxygen or sulfur;

V is $CH_2$, CO, CS, $SO_2$, $CH(C_1$–$C_6$ alkyl), $CH(C_3$–$C_7$ cycloalkyl), with the proviso that V may not be CO, CS or $SO_2$ when $A^2$ is $SO_2$, oxygen or sulfur; and Y is a bond or $C_1$–$C_6$ alkylene; or

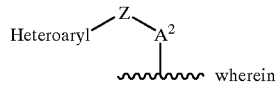

wherein

X is
heteroaryl is 2-, 3- or 4-pyridyl, 2-, 4- or 5-pyrimidinyl, 1-, 2- or 4-imidazolyl, 2-, 4-, or 5-oxazolyl, 1-, 3- , or 5-thiazolyl, 1-, 3- or 4-pyrazolyl, 1-, 3- or 4-triazolyl, 2-pyrazinyl, or 1-, 2- or 5-tetrazolyl, each of which is optionally mono- or di-substituted with halogen, trifluoromethyl, amino, $C_1$–$C_6$ alkylamino, $C_1$–$C_6$ dialkylamino, $C_3$–$C_7$ cycloalkylamino, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, $C_3$–$C_7$ cycloalkoxy, with the proviso that tetrazolyl may have at most one substituent;

Z is $C_1$–$C_6$ alkylene; and $A^2$ is NH, $SO_2$, oxygen or sulfur.

As the compounds of Formula I are effective neuropeptide Y1 receptor antagonists, these compounds are useful in the treatment of a wide variety of clinical conditions which are characterized by the presence of an excess of neuropeptide Y.

DETAILED DESCRIPTION OF THE INVENTION

The novel compounds encompassed by the instant invention can be described by general Formula I:

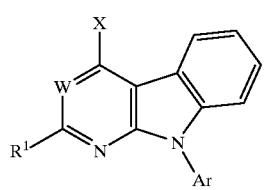

I wherein:
Ar is phenyl, 1- or 2-naphthyl, 2-, 3-, or 4-pyridyl, 2-, 4- or 5-pyrimidinyl, each of which is optionally mono-, di-, or trisubstituted with halogen, trifluoromethyl, hydroxy, amino, $C_1$–$C_6$ alkylamino, $C_1$–$C_6$ dialkylamino, $C_3$–$C_7$ cycloalkylamino, carboxamido, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, $C_3$–$C_7$ cycloalkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, ($C_3$–$C_7$ cycloalkyl) $C_1$–$C_6$ alkyl, $C_3$–$C_7$ cycloalkyl, or ($C_1$–$C_6$ alkylene)—$G^1$—$R^2$ wherein $G^1$ is oxygen or sulfur and $R^2$ is hydrogen, $C_1$–$C_6$ alkyl, or $C_3$–$C_7$ cycloalkyl;

W is N or C—$R^3$, wherein $R^3$ is hydrogen or $C_1$–$C_6$ alkyl;

X is

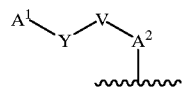

wherein
$A^1$ is $NR^4R^5$ wherein $R^4$ and $R^5$ are independently hydrogen, a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;
$C_1$–$C_6$ alkanoyl, ($C_3$–$C_7$ cycloalkyl) $C_1$–$C_6$ alkanoyl, $C_3$–$C_7$ cycloalkanoyl, $C_1$–$C_6$ alkylsulfonyl, or $C_3$–$C_7$ cycloalkylsulfonyl with the proviso that $R^4$ and $R^5$ may not both be alkanoyl or alkylsulfonyl;
$C_1$–$C_6$ heterocycloalkyl, wherein heterocycloalkyl is morpholinyl, piperazinyl, piperidinyl, or pyrrolidinyl;
$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, $C_1$–$C_6$ dialkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where 2 adjacent substituents may together form a 5-7 fused cycloalkyl or heterocycloalkyl ring;
$NR^4R^5$ taken together form a $C_3$–$C_6$ heterocycloalkyl, or a group of the formula:

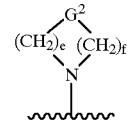

wherein e and f are independently 1, 2, or 3 and the sum of e and f is at least 3; and $G^2$ is
(i) $NR^6$ wherein $R^6$ is hydrogen, $C_1$–$C_6$ alkyl, ($C_3$–$C_7$ cycloalkyl) $C_1$–$C_6$ alkyl, or $C_3$–$C_7$ cycloalkyl; or
(ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—,—NH($C_3$–$C_7$ cycloalkyl)—, where $R^7$ is hydrogen, $C_1$–$C_6$ alkyl, ($C_3$–$C_7$ cycloalkyl) $C_1$–$C_6$ alkyl, or $C_3$–$C_7$ cycloalkyl; or (iii) —CONH$_2$—, or —CO[N($C_1$–$C_6$ alkylene)$R^8$]— wherein $R^8$ is hydrogen, $C_1$–$C_6$ alkyl, ($C_3$–$C_7$ cycloalkyl) $C_1$–$C_6$ alkyl, or $C_3$–$C_7$ cycloalkyl;

$A^2$ is NH, SO$_2$, oxygen or sulfur;

V is CH$_2$, CO, CS, SO$_2$, CH($C_1$–$C_6$ alkyl), CH($C_3$–$C_7$ cycloalkyl), with the proviso that V cannot be CO, CS or SO$_2$ when $A^2$ is SO$_2$, oxygen or sulfur; and Y is a bond or $C_1$–$C_6$ alkylene; or Heteroaryl—Z—$A^2$ wherein X is heteroaryl is 2-, 3- or 4-pyridyl, 2-, 4- or 5-pyrimidinyl, 1-, 2- or 4-imidazolyl, 2-, 4-, or 5-oxazolyl, 1-, 3-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or di-substituted with halogen, trifluoromethyl, amino, $C_1$–$C_6$ alkylamino, $C_1$–$C_6$ dialkylamino, $C_3$–$C_7$ cycloalkylamino, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, or $C_3$–$C_7$ cycloalkoxy, with the proviso that tetrazolyl can have at most one substituent;

Z is $C_1$–$C_6$ alkylene; and
$A^2$ is NH, SO$_2$, oxygen or sulfur.

Preferred compounds of Formula I include those of the following formula:

where E is nitrogen or CH;
each $R_a$ is independently $C_1$–$C_6$ alkyl;
$R_1$ is $C_1$–$C_3$ alkyl; and
t is 0, 1, 2, or 3; and
$R_n$ is $C_1$–$C_6$ alkyl.

Other preferred compounds of Formula I include those of the following formula:

where
W is CH or N, preferably N;
$R_x$ and $R_y$ are alkyl; or

NR$_x$R$_y$ represents pyrrolidinyl, piperidyl, or piperazinyl;
each $R_a$ is independently $C_1$–$C_6$ alkyl;
$R_1$ is $C_1$–$C_3$ alkyl; and
t is 1, 2 or 3.

Other preferred compounds of Formula I include those of the following formula:

where
W is N or CH, preferably N;
E is nitrogen or CH, preferably CH;
each $R_a$ is independently $C_1$–$C_6$ alkyl;
$R_1$ is $C_1$–$C_3$ alkyl;
t is 0, 1, 2, or 3; and
$R_i$ is $C_1$–$C_6$ alkyl.

Other preferred compounds of Formula I include those of the following formula:

where
W is CH or N, preferably N;
each $R_a$ is independently $C_1$–$C_6$ alkyl;
$R_1$ is $C_1$–$C_3$ alkyl;
t is 1, 2, or 3; and
$R_x$ is selected from di($C_1$–$C_6$)alkoxybenzylcarbonyl; ($C_1$–$C_6$)alkoxybenzylcarbonyl; imidazol-5-ylcarbonyl; pyrazin-2-ylcarbonyl; 2-(di ($C_1$–$C_6$) alkoxyphenyl) ethyl; 2-(trifluoromethylphenyl)ethyl; 2-(($C_1$–$C_6$)alkoxyphenyl) ethyl; 2-(imidazol-5-yl)ethyl; 2-phenylethyl; imidazol-5-ylmethylcarbonyl; cyclopropylcarbonyl; $C_3$–$C_7$ cycloalkyl; 2-methylimidazol-4-ylmethyl; imidazol-5-ylmethyl; $C_1$–$C_6$ alkyl; 2-(morpholin-4-yl)ethyl; (2-($C_1$–$C_3$)alkyl-(1,3-thiazol-4-yl)methyl; (5-halo-2-($C_1$–$C_6$)alkyl-(1,3-thiazol-4-yl)methyl; or (2H,3H-benzo[e]1,4-dioxin-6-yl).

Other preferred compounds of Formula I include those of the following formula:

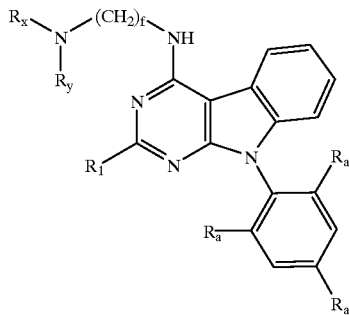

where
- each $R_a$ is independently $C_1$–$C_6$ alkyl;
- $R_1$ is $C_1$–$C_3$ alkyl;
- f is 2, 3, or 4; and
- $NR_xR_y$ represents piperidin-4-yl;
- $R_x$ is hydrogen, and $R_y$ is 2-(morpholin-4-yl)ethyl;
- $R_x$ and $R_y$ are hydrogen; or
- $NR_xR_y$ represents pyrrolidinyl.

Other preferred compounds of Formula I include those of the following formula:

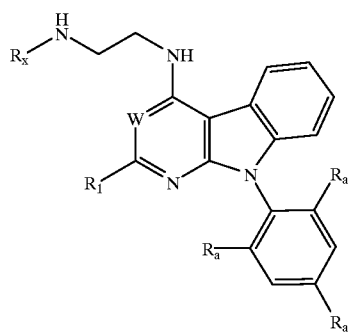

where
- W is CH or N;
- each $R_a$ is independently $C_1$–$C_6$ alkyl;
- $R_1$ is $C_1$–$C_3$ alkyl;
- t is 1, 2, or 3; and
- $R_x$ is $C_1$–$C_6$ alkyl, (ω-($C_1$–$C_6$ alkoxyphenyl) ($C_1$–$C_6$)alkyl; ω-(di($C_1$–$C_6$) alkoxyphenyl) ($C_1$–$C_6$) alkyl; ω-(($C_1$–$C_6$) alkoxy-(cyclopropylmethoxy)phenyl) ($C_1$–$C_6$) alkyl; ω-(($C_1$–$C_6$) alkoxy-($C_1$–$C_6$)cycloalkyloxyphenyl) ($C_1$–$C_6$)alkyl; ω-(($C_1$–$C_6$) alkoxy-hydroxyphenyl) ($C_1$–$C_6$) alkyl; ω-(aminophenyl) ($C_1$–$C_6$) alkyl; ω-(hydroxyphenyl) ($C_1$–$C_6$)alkyl; ω-(imidazol-5-yl) ($C_1$–$C_6$)alkyl; ω-(morpholin-4-yl) ($C_1$–$C_6$)alkyl; ω-phenyl ($C_1$–$C_6$) ($C_1$–$C_6$)alkyl; ω-(2-, 3-, or 4-pyridyl) ($C_1$–$C_6$) alkyl; ω-phenyl ($C_1$–$C_6$) alkyl; ω-phenyl ($C_1$–$C_6$) alkyl; ($C_1$–$C_6$) alkoxybenzyl; cyclopropylmethyl; ($C_3$–$C_7$) cycloalkyl; (dimethylamino)phenylmethyl; (2H,3H-benzo[e]1,4-dioxin-6-yl)carbonylmethyl; 2-((2H,3H-benzo[e]1,4-dioxin-6-yl)carbonyl)ethyl; or 2-(2H-benzo[3,4-d]1,3-dioxolan-5-yl)ethyl; ω-(dimethoxyphenyl) ($C_1$–$C_6$) alkyl.

Other preferred compounds of Formula I include those of the following formula:

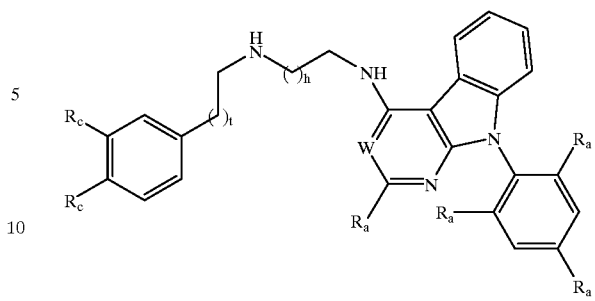

where
- each $R_a$ is independently $C_1$–$C_6$ alkyl or hydrogen, provided that at least one $R_a$ is not hydrogen and is in the 2- or 4-position;
- $R_1$ is $C_1$–$C_3$ alkyl;
- W is CH or N, preferably N,
- t is 0, 1 or 2;
- h is 1, 2, or 3; and
- each $R_c$ is independently hydrogen, $C_1$–$C_6$ alkoxy, or $C_1$–$C_6$ alkyl.

Still other preferred compounds of the invention are those having formula II:

II

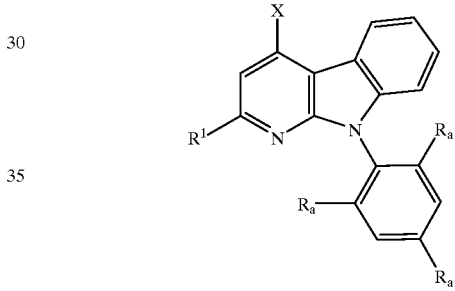

wherein:
- each $R_a$ is independently lower alkyl;
- $R^1$ hydrogen, halogen, trifluoromethyl, $C_1$–$C_6$ alkyl, $C_3$–$C_7$ cycloalkyl, ($C_3$–$C_7$ cycloalkyl) $C_1$–$C_6$ alkyl, or ($C_1$–$C_6$ alkylene)—$G^1$—$R^2$ wherein G is oxygen or sulfur and $R^2$ is hydrogen, $C_1$–$C_6$ alkyl, or $C_3$–$C_7$ cycloalkyl; and
- X is

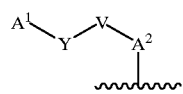

wherein
- $A^1$ is $NR^4R^5$ wherein $R^4$ and $R^5$ are independently hydrogen, a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;
- $C_1$–$C_6$ alkanoyl, ($C_3$–$C_7$ cycloalkyl) $C_1$–$C_6$ alkanoyl, $C_3$–$C_7$ cycloalkanoyl, $C_1$–$C_6$ alkylsulfonyl, or $C_3$–$C_7$ cycloalkylsulfonyl with the proviso that $R^4$ and $R^5$ cannot both be alkanoyl or alkylsulfonyl;
- $C_1$–$C_6$ heterocycloalkyl, wherein heterocycloalkyl is morpholinyl, piperazinyl, piperidinyl, or pyrrolidinyl;
- $C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, $C_1$–$C_6$ dialkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where 2 adjacent substituents may together form a 5-7 fused cycloalkyl or heterocycloalkyl ring;

$NR^4R^5$ taken together form a $C_3$–$C_6$ heterocycloalkyl, or a group of the formula:

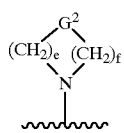

wherein e and f are independently 1, 2, or 3 and the sum of e and f is at least 3; and $G^2$ is
(i) $NR^6$ wherein $R^6$ is hydrogen, $C_1$–$C_6$ alkyl, ($C_3$–$C_7$ cycloalkyl) $C_1$–$C_6$ alkyl, $C_3$–$C_7$ cycloalkyl, or
(ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—, —NH($C_3$–$C_7$ cycloalkyl)—, where $R^7$ is hydrogen, or $C_1$–$C_6$ alkyl, $C_3$–$C_7$ cycloalkyl; or
(iii) —$CONH_2$—, or —$CO[N(C_1$–$C_6$ alkylene)$R^8$]— wherein $R^8$ is hydrogen, $C_1$–$C_6$ alkyl, or $C_3$–$C_7$ cycloalkyl;

$A^2$ is NH, $SO_2$, oxygen or sulfur;
V is $CH_2$, CO, CS, $SO_2$, $CH(C_1$–$C_6$ alkyl), $CH(C_3$–$C_7$ cycloalkyl), with the proviso that V cannot be CO, CS or $SO_2$ when $A^2$ is $SO_2$, oxygen or sulfur; and
Y is a bond or $C_1$–$C_6$ alkylene; or

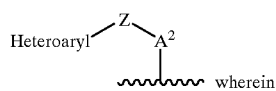
wherein

X is
heteroaryl is 2-, 3- or 4-pyridyl, 2-, 4- or 5-pyrimidinyl, 1-, 2- or 4-imidazolyl, 2-, 4-, or 5-oxazolyl, 1-, 3- , or 5-thiazolyl, 1-, 3- or 4-pyrazolyl, 1-, 3- or 4-triazolyl, 2-pyrazinyl, or 1-, 2- or 5-tetrazolyl, each of which is optionally mono- or di-substituted with halogen, trifluoromethyl, amino, $C_1$–$C_6$ alkylamino, $C_1$–$C_6$ dialkylamino, $C_3$–$C_7$ cycloalkylamino, $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, with the proviso that tetrazolyl may have at most one substituent;

Z is $C_1$–$C_6$ alkylene; and
$A^2$ is NH, $SO_2$, oxygen or sulfur.

Preferred compounds of Formula II are those where $R^1$ is $C_1$–$C_6$ alkyl and each $R_a$ is methyl. Other preferred compounds of Formula II are those where V is $CH_2$, Y is $C_1$–$C_6$ alkyl and $A^1$ is
$NR^4R^5$ wherein $R^4$ and $R^5$ are independently hydrogen, a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;

$C_1$–$C_6$ alkanoyl, ($C_3$–$C_7$ cycloalkyl) $C_1$–$C_6$ alkanoyl, $C_3$–$C_7$ cycloalkanoyl, $C_1$–$C_6$ alkylsulfonyl, or $C_3$–$C_7$ cycloalkylsulfonyl with the proviso that $R^4$ and $R^5$ cannot both be alkanoyl or alkylsulfonyl;

$C_1$–$C_6$ heterocycloalkyl, wherein heterocycloalkyl is morpholinyl, piperazinyl, piperidinyl, or pyrrolidinyl;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, $C_1$–$C_6$ dialkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy; or $NR^4R^5$ taken together form a $C_3$–$C_6$ heterocycloalkyl, or a group of the formula:

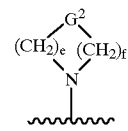

wherein e and f are independently 1, 2, or 3 and the sum of e and f is at least 3; and $G^2$ is
(i) $NR^6$ wherein $R^6$ is hydrogen, $C_1$–$C_6$ alkyl, ($C_3$–$C_7$ cycloalkyl) $C_1$–$C_6$ alkyl, or $C_3$–$C_7$ cycloalkyl, or
(ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—, —NH($C_3$–$C_7$ cycloalkyl)—, and $R^7$ is hydrogen, $C_1$–$C_6$ alkyl, $C_3$–$C_7$ cycloalkyl; or
(iii) —$CONH_2$—, or —$CO[N(C_1$–$C_6$ alkylene)$R^8$]— wherein $R^8$ is hydrogen, $C_1$–$C_6$ alkyl, or $C_3$–$C_7$ cycloalkyl.

Yet other preferred compounds of the invention are those of Formula III:

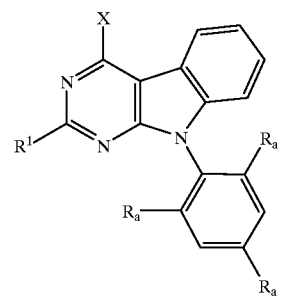

III wherein:
each $R_a$ is independently lower alkyl;
$R^1$ is hydrogen, halogen, trifluoromethyl, $C_1$–$C_6$ alkyl, or ($C_1$–$C_6$ alkylene)—$G^1$—$R^2$ wherein $G^1$ is oxygen or sulfur and $R^2$ is hydrogen or $C_1$–$C_6$ alkyl; and X is

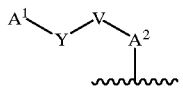

wherein $A^1$ is $NR^4R^5$ wherein $R^4$ and $R^5$ are independently hydrogen or a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;

$C_1$–$C_6$ alkanoyl, ($C_3$–$C_7$ cycloalkyl) $C_1$–$C_6$ alkanoyl, $C_3$–$C_7$ cycloalkanoyl, $C_1$–$C_6$ alkylsulfonyl, or $C_3$–$C_7$ cycloalkylsulfonyl, with the proviso that $R^4$ and $R^5$ cannot both be alkanoyl or alkylsulfonyl;

$C_1$–$C_6$ heterocycloalkyl, wherein heterocycloalkyl is morpholinyl, piperazinyl, piperidinyl, or pyrrolidinyl;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, $C_1$–$C_6$ dialkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where any 2 adjacent substituents may together form a 5-7 fused cycloalkyl or heterocycloalkyl ring; or $NR^4R^5$ taken together form a $C_3$–$C_6$ heterocycloalkyl, or a group of the formula:

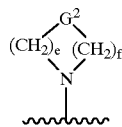

wherein e and f are independently 1, 2, or 3 and the sum of e and f is at least 3; and $G^2$ is
  (i) $NR^6$ wherein $R^6$ is hydrogen, $C_1$–$C_6$ alkyl, ($C_3$–$C_7$ cycloalkyl) $C_1$–$C_6$ alkyl, or $C_3$–$C_7$ cycloalkyl, or
  (ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—, —NH($C_3$–$C_7$ cycloalkyl)—, and $R^7$ is hydrogen, $C_1$–$C_6$ alkyl, $C_3$–$C_7$ cycloalkyl; or
  (iii) —$CONH_2$—, or —$CO[N(C_1$–$C_6$ alkylene)$R^8$]— wherein $R^8$ is hydrogen, $C_1$–$C_6$ alkyl, or $C_3$–$C_7$ cycloalkyl;

$A^2$ is NH or oxygen;

V is $CH_2$, CO, CS, $SO_2$ or $CH(C_1$–$C_6$ alkyl), with the proviso that V cannot be CO, CS or $SO_2$ when $A^2$ is $SO_2$, oxygen or sulfur; and Y is a bond or $C_1$–$C_6$ alkyl; or

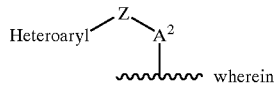

wherein

X is heteroaryl is 2-, 3- or 4-pyridyl, 2-, 4- or 5-pyrimidinyl, 1-, 2- or 4-imidazolyl, 2-, 4-, or 5-oxazolyl, 1-, 3- or 4-pyrazolyl, 1-, 3- or 4-triazolyl, 2-pyrazinyl, or 1-, 2- or 5-tetrazolyl, each of which is optionally mono- or di-substituted with halogen, trifluoromethyl, amino, $C_1$–$C_6$ alkyl, $C_1$–$C_6$ alkoxy, ($C_3$–$C_7$ cycloalkyl) $C_1$–$C_6$ alkoxy, with the proviso that tetrazole may have at most one substituent;

Z is $C_1$–$C_6$ alkylene; and $A^2$ is NH, or oxygen.

Preferred compounds of Formula III are those where $R^1$ is $C_1$–$C_6$ alkyl and each $R_a$ is methyl. Other preferred compounds of Formula III are those where $A^1$ is $NR^4R^5$ wherein $R^4$ is hydrogen and $R^5$ is a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;

$C_1$–$C_6$ heterocycloalkyl, wherein heterocycloalkyl is morpholinyl, piperazinyl, piperidinyl, or pyrrolidinyl;

$C_1$–$C_6$ arylalkyl where aryl is phenyl, 2-,3-, or 4-pyridyl, 2-, 4- or 5-pyrimidinyl, each of which is optionally mono-, di-, or tri-substituted with halogen, trifluoromethyl, hydroxy, amino, $C_1$–$C_6$ alkylamino, $C_1$–$C_6$ dialkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where any 2 adjacent substituents may together form a 5-7 fused cycloalkyl or heterocycloalkyl ring;

$NR^4R^5$ taken together form a $C_3$–$C_6$ heterocycloalkyl, or a group of the formula:

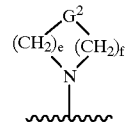

wherein e and f are independently 1, 2, or 3 and the sum of e and f is at least 3; and $G^2$ is
  (i) $NR^6$ wherein $R^6$ is hydrogen, $C_1$–$C_6$ alkyl, ($C_3$–$C_7$ cycloalkyl) $C_1$–$C_6$ alkyl, or $C_3$–$C_7$ cycloalkyl; or
  (ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—and $R^7$ is hydrogen or $C_1$–$C_6$ alkyl; or
  (iii) —$CONH_2$—, or —$CO[N(C_1$–$C_6$ alkylene)$R^8$]— wherein $R^8$ is hydrogen or $C_1$–$C_6$ alkyl;

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Examples 1–122 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "alkyl", "lower alkyl", or $C_1$–$C_6$ alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl.

By "cycloalkyl", "lower cycloalkyl", or $C_3$–$C_7$ cycloalkyl in the present invention is meant alkyl groups having 3–7 carbon atoms forming a ring, such as, for example, cyclopropyl, cyclobutyl, cyclopentyl, cyclohexyl, or cycloheptyl.

By "(cycloalkyl) alkyl", "lower (cycloalkyl)alkyl", or ($C_3$–$C_7$ cycloalkyl) $C_1$–$C_6$ alkyl in the present invention is meant a straight or branched alkyl substituent formed of 1 to 6 carbon atoms attached to a cycle having 3–7 carbon atoms, such as, for example, cyclopropylmethyl, cyclobutylmethyl, cyclopentylmethyl, cyclohexylmethyl, cycloheptylmethyl, and the like.

By "alkoxy", "lower alkoxy", $C_1$–$C_6$ alkoxy, or $C_1$–$C_6$ alkyloxy in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "cycloalkoxy", "lower cycloalkoxy", $C_3$–$C_7$ cycloalkoxy, or $C_3$–$C_7$ cycloalkyloxy in the present invention is meant a group formed by an oxygen atom attached to a cycle having 3–7 carbon atoms, such as, for example, cyclopropoxy, cyclobutoxy, cyclopentoxy, cyclohexoxy, or cycloheptoxy.

By "(cycloalkyl)alkyloxy", "lower (cycloalkyl)alkyloxy", ($C_3$–$C_7$ cycloalkyl) $C_1$–$C_6$ alkoxy, or ($C_3$–$C_7$ cycloalkyl) $C_1$–$C_6$ alkyloxy in the present invention is meant a group formed by an oxygen atom attached to a 1–6 carbon chain linked to a cycle of 3–7 carbon atoms, such as, for example, cyclopropylmethyloxy, cyclobutylmethyloxy, cyclopentylmethyloxy, cyclohexylmethyloxy, cycloheptylmethyloxy, and the like.

CONH represents an amide functional group, i.e.,

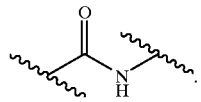

The term "heterocycle" or "heterocycloalkyl" means a monocyclic or bicyclic hydrocarbon group which in which one or more of the ring carbon atoms has been replaced with a heteroatom, e.g., oxygen, sulfur or nitrogen. Such groups preferably have 4 to 10 carbon atoms and 1 to 4 heteroatoms.

By the term "halogen" in the present invention is meant fluorine, bromine, chlorine, and iodine.

As the compounds of Formula I are effective neuropeptide Y1 (NPY1) receptor antagonists, these compounds are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders may include: disorders or diseases pertaining to the heart, blood vessels or the renal system, such as vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport, or renal failure; conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia; conditions related to pain or nociception; diseases related to abnormal gastrointestinal motility and secretion, such as different forms of ileus, urinary incontinence, and Crohn's disease; abnormal drink and food intake disorders, such as obesity, anorexia, bulimia, and metabolic disorders; diseases related to sexual dysfunction and reproductive disorders; conditions or disorders associated with inflammation; respiratory diseases, such as asthma and conditions related to asthma and bronchoconstriction; and diseases related to abnormal hormone release, such as leutinizing hormone, growth hormone, insulin, and prolactin. See U.S. Pat. No. 5,504,094.

The interaction of the aminoalkyl substituted 9H-pyridino [2,3-b]indole and 9H-pyrimidino[4,5-b]indole derivatives of the invention with NPY receptors is shown in the examples. This interaction results in the pharmacological activities of these compounds as illustrated in relevant animal models.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachid oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preparation of Aminoalkyl Substituted 9H-Pyridino [2,3-b]indole and 9H-Pyrimidino[4,5-b]indole Derivatives An illustration of preparation methods of compounds of the present invention is given in Schemes I–XIII. Those having skill in the art will recognize that the starting materials may be varied and additional steps employed to produce compounds encompassed by the present invention.

Scheme I

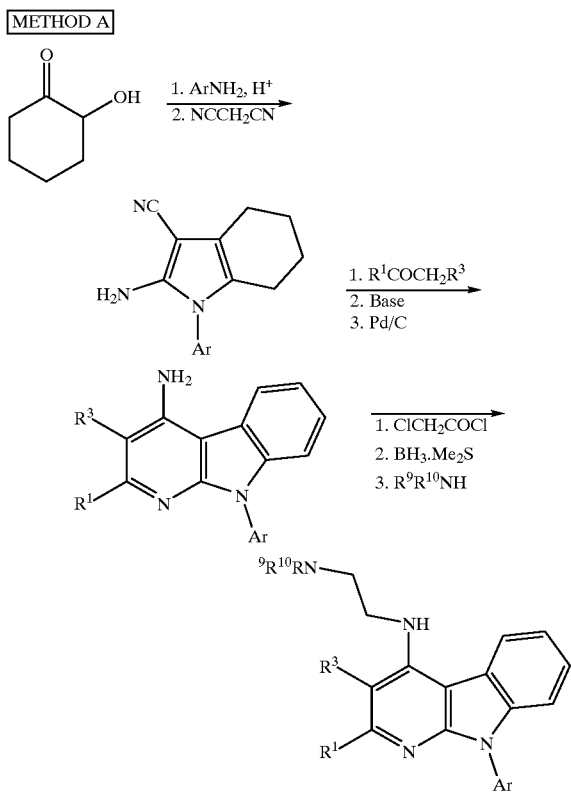

In Scheme I, Ar, $R^1$ and $R^2$ are as defined above for Formula I; and the group NH—$(CH_2)_2$—$NR^9R^{10}$ falls within the definition of X and is substituted according to the definition of X in Formula I.

Scheme II

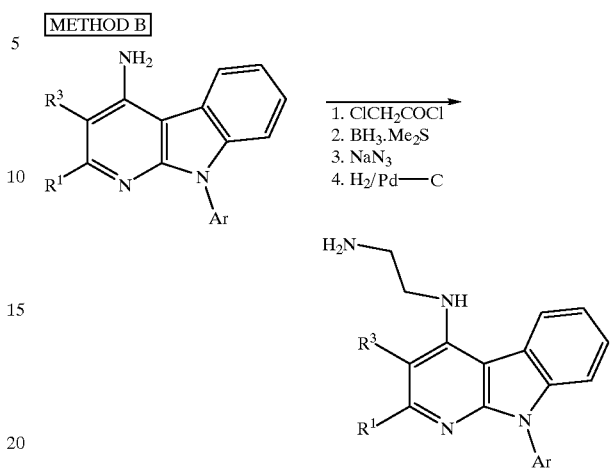

In Scheme II, Ar, $R^1$ and $R^3$ are as defined above for Formula I; and the group NH—$(CH_2)_2$—$NH_2$ falls within the definition of X and is substituted according to the definition of X in Formula I.

Scheme III

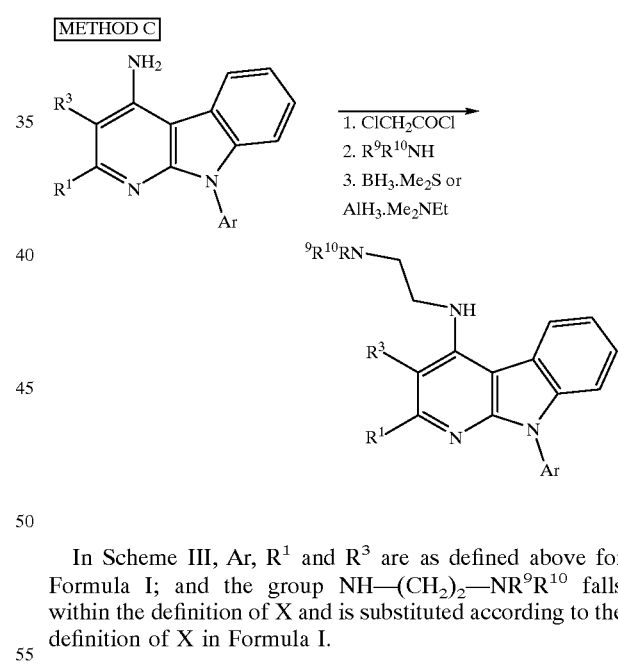

In Scheme III, Ar, $R^1$ and $R^3$ are as defined above for Formula I; and the group NH—$(CH_2)_2$—$NR^9R^{10}$ falls within the definition of X and is substituted according to the definition of X in Formula I.

Scheme IV

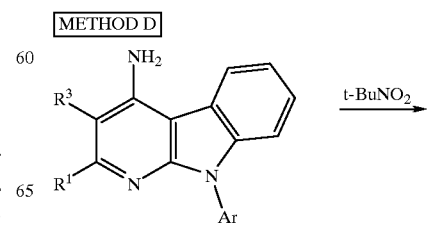

-continued

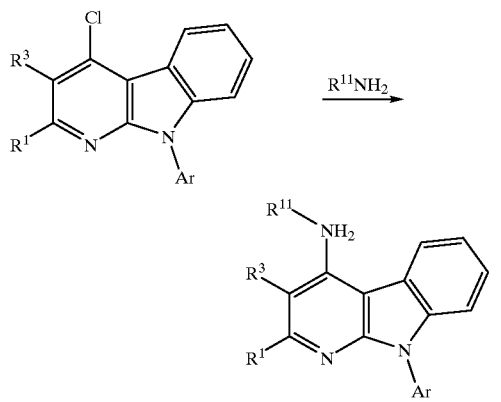

Scheme VI

METHOD F

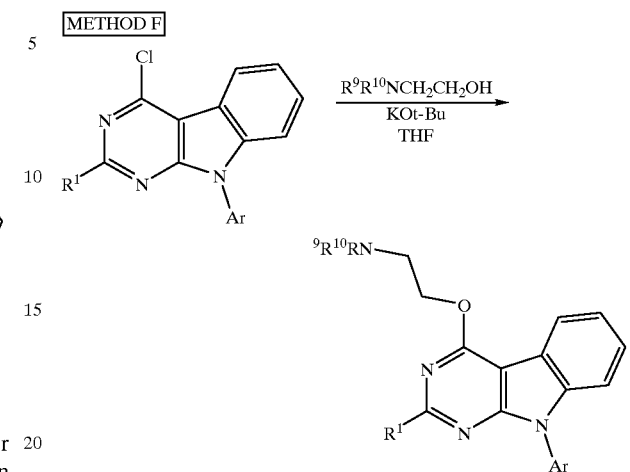

In Scheme IV, Ar, $R^1$ and $R^3$ are as defined above for Formula I; and the group NH—$R^{11}$ falls within the definition of X and is substituted according to the definition of X in Formula I.

In Scheme VI, Ar and $R^1$ are as defined above for Formula I; and the group O—$(CH_2)_2$—$NR^9R^{10}$ falls within the definition of X and is substituted according to definition of X in Formula I.

Scheme V

METHOD E

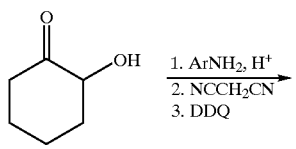

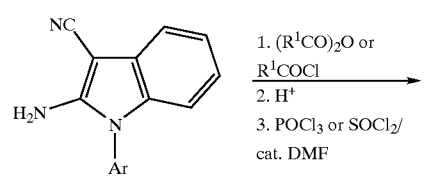

Scheme VII

METHOD G

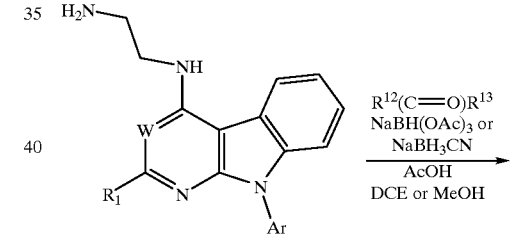

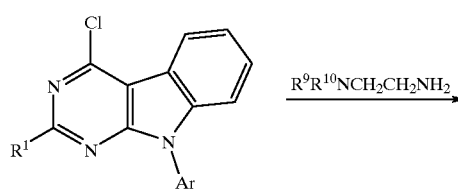

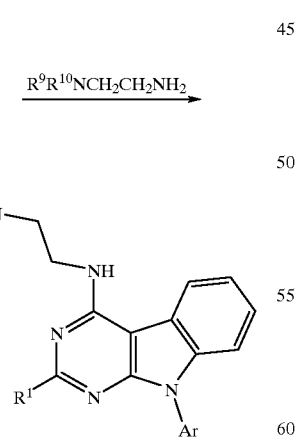

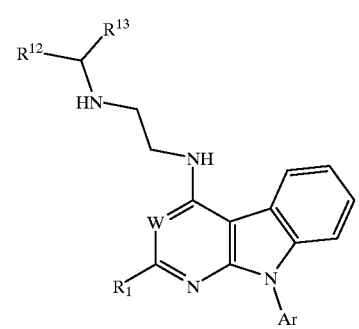

In Scheme V, Ar and $R^1$ are as defined above for Formula I; and the group NH—$(CH_2)_2$—$NR^9R$ falls within the definition of X and is substituted according to the definition of X in Formula I.

In Scheme VII, Ar, $R^1$ and W are as defined above for Formula I; and the group NH—$(CH_2)_2$—NH—$CHR^{12}R^{13}$ falls within the definition of X and is substituted according to the definition of X in Formula I.

Scheme VIII

METHOD H

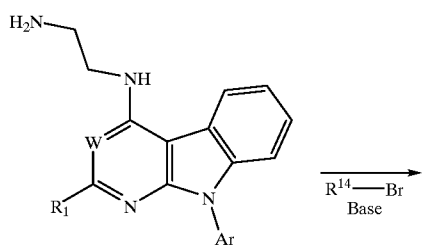

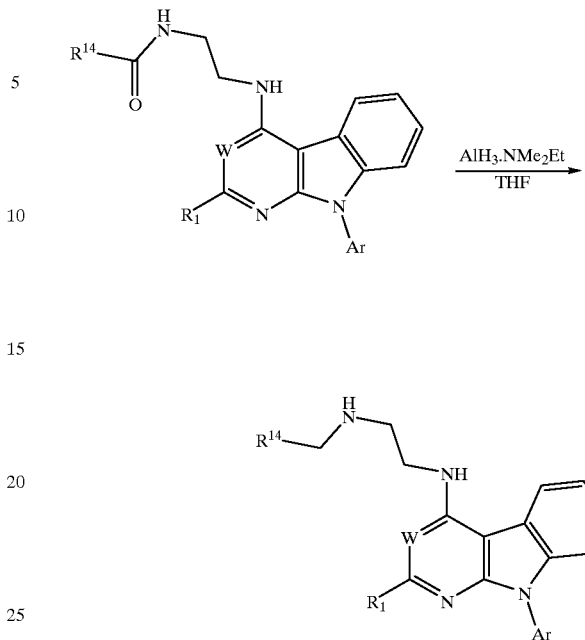

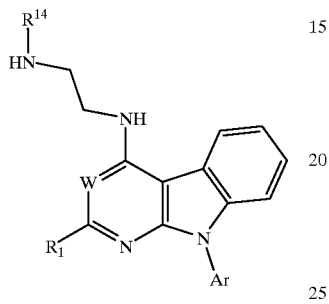

In Scheme VIII, Ar, $R^1$, and W are as defined above for Formula I; and the group NH—$(CH_2)_2$—$NHR^{14}$ falls within the definition of X and is substituted according to the definition of X in Formula I.

Scheme IX

METHOD I

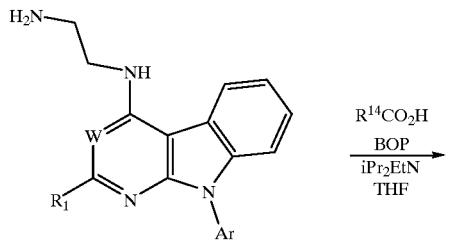

In Scheme IX, Ar, $R^1$, and W are as defined above for Formula I; and the group NH—$(CH_2)_2$—NH—$CH_2R^{14}$ falls within the definition of X and is substituted according to the definition of X in Formula I.

Scheme X

METHOD J

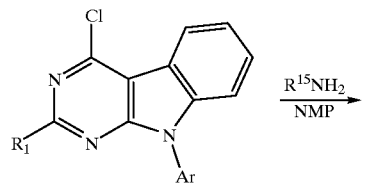

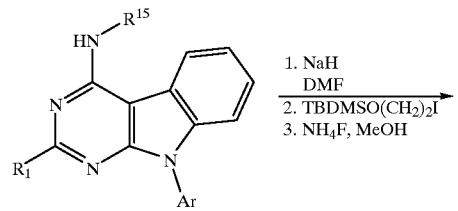

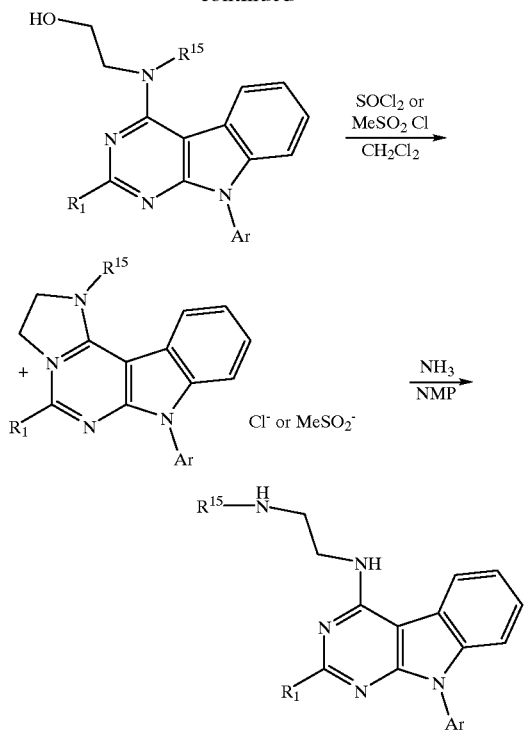

In Scheme X, Ar, and $R^1$ are as defined above for Formula I; and the group $NH-(CH_2)_2-NHR^{15}$ falls within the definition of X and is substituted according to the definition of X in Formula I.

Scheme XI

METHOD K

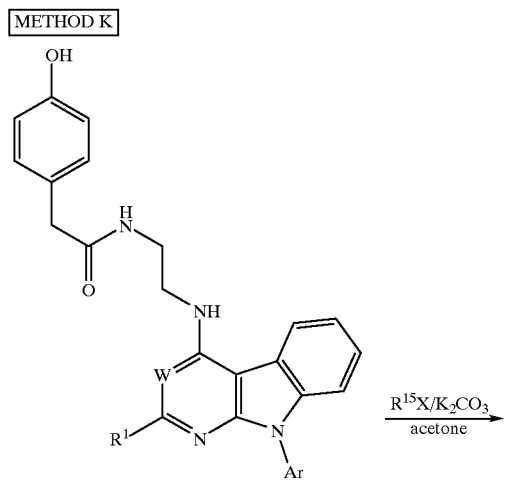

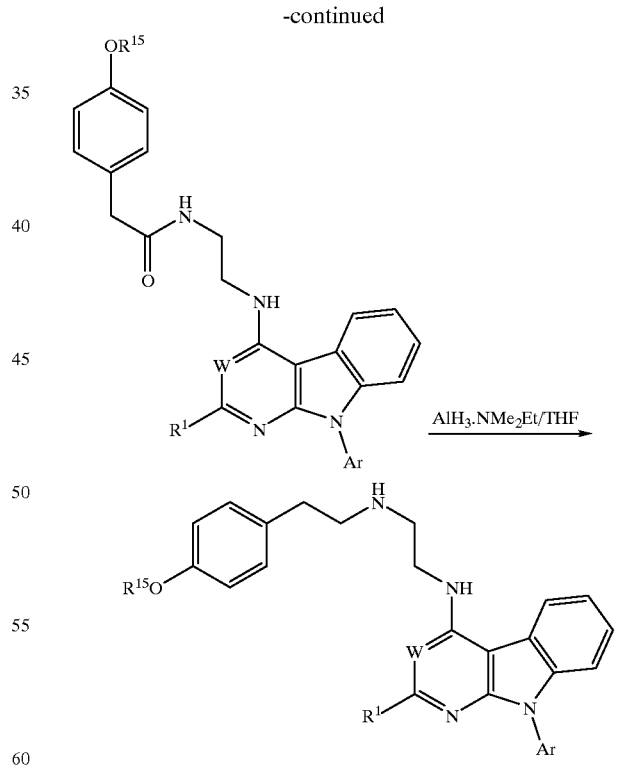

In Scheme XI, Ar, $R^1$, and W are as defined above for Formula I; and the group $NH-(CH_2)_2-NH-(CH_2)_2-Ph-OR^{16}$ falls within the definition of X and is substituted according to the definition of X in Formula I.

Scheme XII

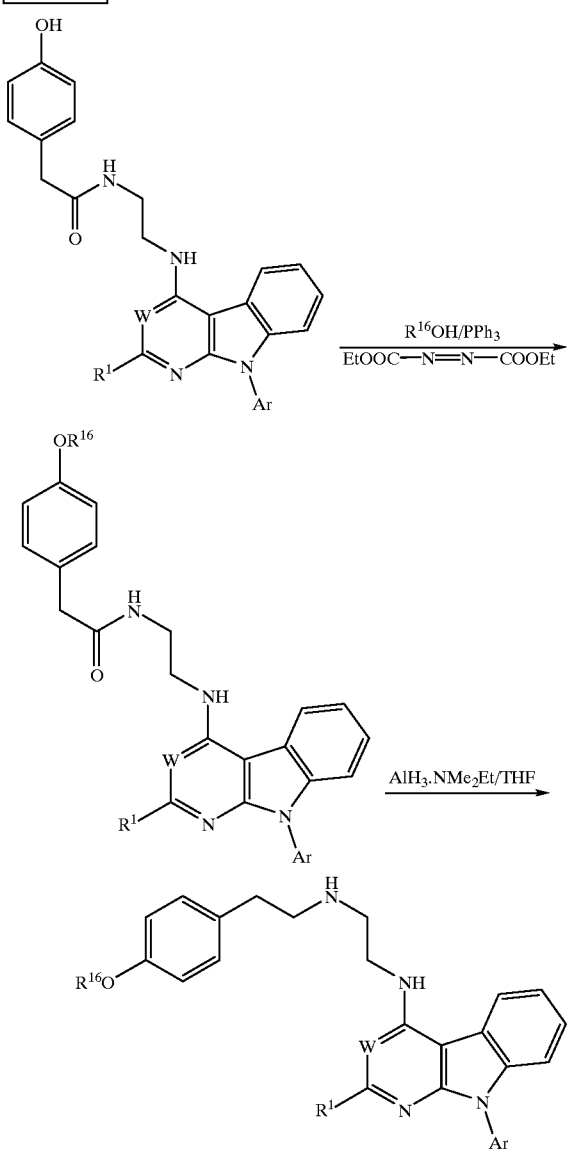

In Scheme XII, Ar, $R^1$, and W are as defined above for Formula I; and the group $NH-(CH_2)_2-NH-(CH_2)_2-Ph-OR^{16}$ falls within the definition of X and is substituted according to the definition of X in Formula I.

Scheme XIII

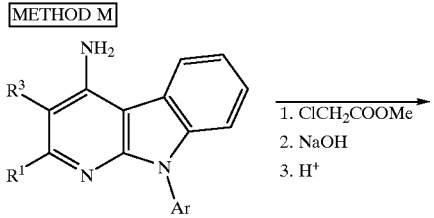

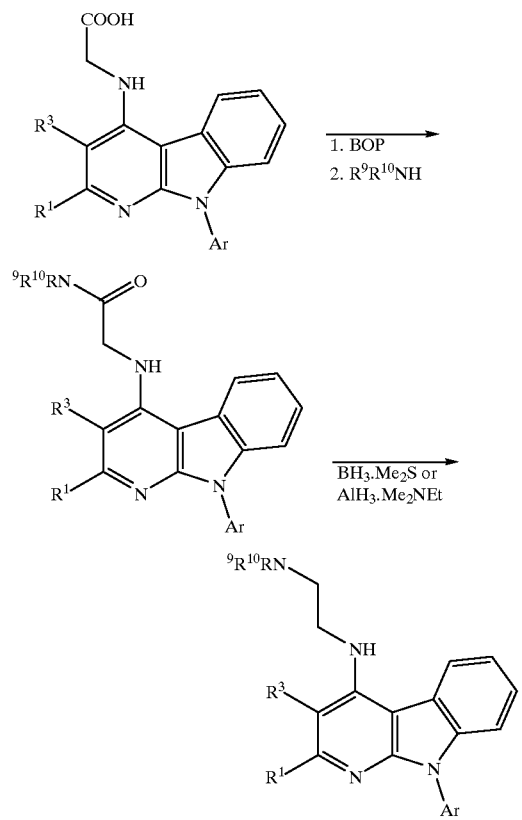

In Scheme XIII, Ar, $R^1$ and $R^3$ are as defined above for Formula I; and the group $NH-(CH_2)_2-NR^9R^{10}$ falls within the definition of X and is substituted according to the definition of X in Formula I.

The disclosures of all articles and references mentioned in this application, including patents, are incorporated herein by reference.

The preparation of the compounds of the present invention is illustrated further by the following examples, which are not to be construed as limiting the invention in scope or spirit to the specific procedures and compounds described in them.

Commercial reagents were used without further purification. THF refers to tetrahydrofuran. LDA refers to lithium diisopropylamide and DDQ refers to 2,3-dichloro-5,6-dicyano-1,4-benzoquinone. Room or ambient temperature refers to 20 to 25° C. Concentration implies the use of a rotary evaporator. TLC refers to thin layer chromatography. Mass spectral data were obtained either by CI or APCI methods.

EXAMPLE 1 (METHOD A)

A. 2-Amino-4,5,6,7-tetrahydro-1-phenyl-1H-indole-3-carbonitrile

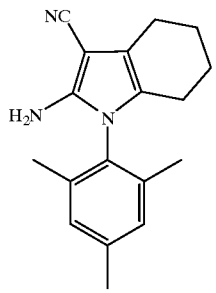

A mixture of 2,4,6-trimethylaniline (500 g) and adipoin (464 g) in toluene (2.5 L) is heated to reflux. A theoretical amount of water is removed azeotropically over the course of 3 hours. The mixture is cooled to ambient temperature, then malononitrile (244 g) and ammonium acetate (57 g) are added. The reaction is slowly re-heated back to reflux for about 1 hour with azeotropic removal of water. After cooling, the precipitate that forms overnight is collected by filtration. The dark solid is washed with ethanol and dried to afford 540 g of a white powder: MS 280 (M+H).

B. 4-Amino-2-methyl-9-(2,4,6-trimethylphenyl)-5,6,7,8-tetrahydro-9H-pyridino[2,3-b]indole

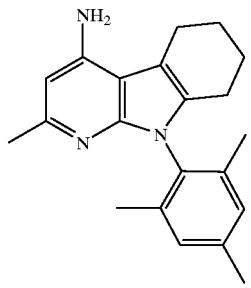

To the product of Example 1A (535 g) dissolved in dichloroethane (4 L) are added 2-methoxypropene (550 mL) and p-toluenesulfonic acid monohydrate (3.6 g). The mixture is refluxed for 1 hour then the solvent is removed by distillation. The residue is dissolved in THF (3 L) and cooled to 0° C. To this solution, under an atmosphere of nitrogen gas, is added LDA (2.0M, 1.2 L) at a rate to keep the reaction's internal temperature below 10° C. After 3 hours the reaction is neutralized with aqueous HCl. The aqueous layer is extracted with ethyl acetate and combined with the THF layer. The combined organic phase is extracted with 3M HCl and the latter is made alkaline (pH=10) with 10N NaOH and ice. The aqueous solution is extracted with dichloromethane, dried over anhydrous sodium sulfate, filtered and concentrated to give a crystalline solid: MS 320 (M+H).

C. 4-Amino-2-methyl-9-(2,4,6-trimethylphenyl)-9H-pyridino[2,3-b]indole

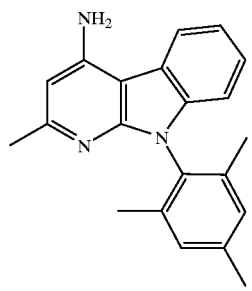

The product of Example 1B (600 g) is dissolved in decahydronaphthalene (4 L) and heated to distill off low boiling impurities that are present. The solution is cooled to ambient temperature and charged with 10% Palladium on Carbon (250 g) under a blanket of argon gas. The mixture is heated to the reflux temperature of 191–193° C. for 9 hours to afford aromatized product. The cooled mixture is diluted with dichloromethane and filtered through a pad of celite. The dichloromethane in the filtrate is removed under reduced vacuum. The remaining decahydronaphthalene solution is treated by bubbling in a stream of hydrochloric acid gas with ice-cooling for about 5 minutes. The solids are filtered, washed with diethyl ether and dried to yield 580 g of product as the HCl salt. The salt is recrystallized from an ethyl acetate and ethanol mixture to give a white product: MS(free base) 316 (M+H).

D. 4-N-((1-Oxo-2-chloro) ethyl)amino-2-methyl-9-(2,4,6-trimethylphenyl)-9H-pyridino[2,3-b]indole

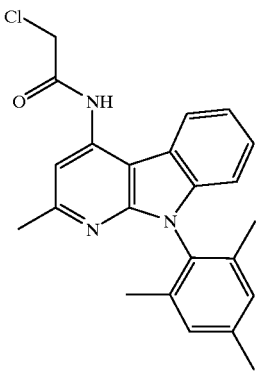

A solution of the compound from Example 1C (10.0 g), chloroacetyl chloride (6.2 mL) and N,N-diisopropylethylamine (4.6 mL) in dichloroethane (100 mL) is refluxed for 2 hours. After concentrating the mixture, aqueous sodium carbonate is added and product is extracted with dichloromethane. The extract is dried over anhydrous sodium sulfate, filtered and concentrated to give the title compounds, which is used directly.

E. 4-N-(2-Chloroethyl)amino-2-methyl-9-(2,4,6-trimethylphenyl)-9H-pyridino[2,3-b]indole

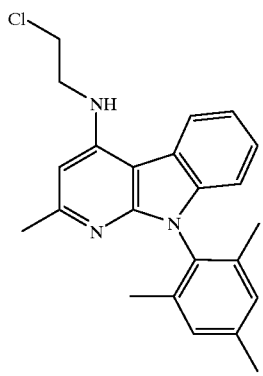

The compound from Example 1D is dissolved in THF (100 mL) and borane-methyl sulfide complex (10M, 3.0 mL) is added. The solution is refluxed for 2 hours, then allowed to cool before carefully quenching with a large excess of methanol (50 mL). The mixture is re-heated to reflux for 1 hour and concentrated to give a viscous oil: MS 378 (M+H).

F. 4-(2-(2-(4-Methoxyphenyl)ethylamino)ethyl)amino-2-methyl-9-(2,4,6-trimethylphenyl)-9H-pyridino[2,3-b]indole

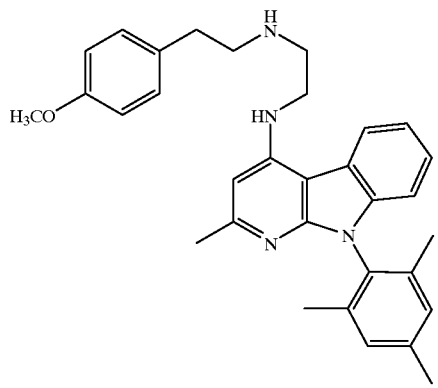

Dissolve the product from Example 1E (1.6 g) in N-methylpyrrolidinone (10 mL) and add 4-methoxyphenethylamine (3 mL). The mixture is heated to 90° C. for 6 hours then poured into water and extracted with ethyl acetate. The organic layer is washed with water, dried over anhydrous sodium sulfate, filtered and concentrated. The product is purified by flash chromatography, using 50% ethyl acetate in hexanes as the eluting solvent, to give a white solid: MS 493 (M+H).

EXAMPLE 2 (METHOD B)

4-(2-Amino-2-methylethyl)amino-2-methyl-9-(2,4,6-trimethylphenyl)-9H-pyridino[2,3-b]indole

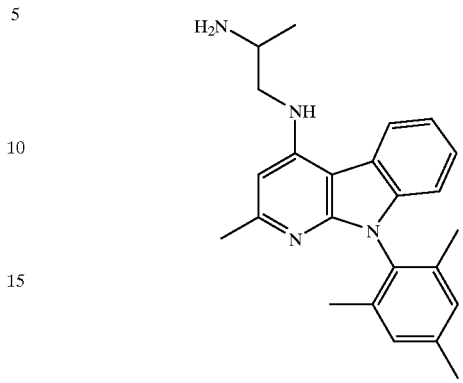

A solution of the product from Example 1C (500 mg) and 2-chloropropionyl chloride (1.5 mL) in dichloroethane (15 mL) is refluxed for 4 hours. The mixture is concentrated and dissolved in dichloromethane. Then, wash with aqueous sodium carbonate solution, dry over anhydrous sodium sulfate, filter and concentrate. The acylated product is dissolved in THF and reduced by adding borane-methyl sulfide complex (10M, 5 mL) and stirring for 10 hours at room temperature. The mixture is quenched with a large excess of methanol and concentrated. The latter product is dissolved in N-methylpyrrolidinone (5 mL) containing sodium azide (350 mg) and heated to 120° C. for 4 hours. The mixture is poured into water and extracted with ethyl acetate. The organic layer is washed with water, dried over anhydrous sodium sulfate, filtered and concentrated. The azide product is dissolved in ethanol (15 mL) with 10% palladium on carbon (about 300 mg) and hydrogenated for 8 hours at approximately 1 atmosphere pressure. The suspension is filtered over celite and the concentrated product is purified by preparative TLC. First elute TLC plate with ethyl acetate, then 10% methanol in dichloromethane to obtain a racemic mixture of the purified product: MS 373 (M+H).

EXAMPLE 3 (METHOD B)

4-(2-Aminoethyl)amino-2-methyl-9-(2,4,6-trimethylphenyl)-9H-pyridino[2,3-b]indole

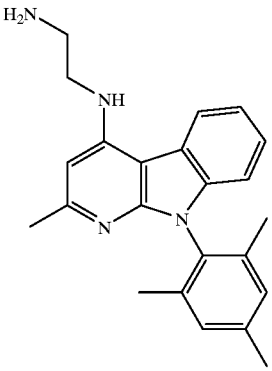

A solution of the compound from example 1E (2.80 g, 7.41 mmol) in N-methylpyrrolidinone (50 mL) is treated with sodium azide (0.506 g, 7.78 mmol). The mixture is heated at 70° C. for 24 hours. The resulting mixture is cooled to room temperature, poured into water, and extracted twice with ethyl acetate. The combined extracts are washed thoroughly with water then saturated NaCl solution, dried over anhydrous sodium sulfate, filtered and concentrated to give the azide intermediate which is used without further purification.

A solution of this azide (2.85 g, 7.42 mmol), 10% Pd on carbon (0.3 g) and ethanol (50 mL) is treated with hydrogen gas in the Parr shaker for 8 hours. The solution is filtered through Celite which is washed with several portions of dichloromethane. The filtrate is concentrated in vacuo to dryness and the residue purified by flash column chromatography, eluting with 5% methanol-dichloromethane, to give the title product as a gray solid.

EXAMPLE 4 (Method C)

A. 4-(2-Dimethylamino-1-oxoethyl)amino-2-methyl-9-(2,4,6-trimethylphenyl)-9H-pyridino[2,3-b]indole

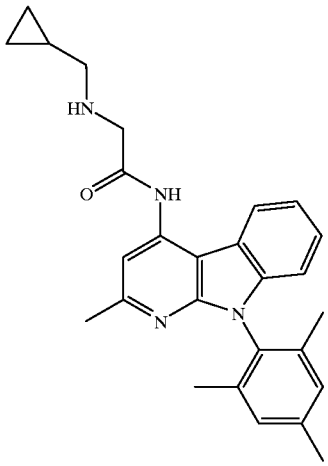

To a N-methyl pyrrolidinone (NMP) solution of the product from Example 1D (0.1 mL of a 0.2 M solution) is added cyclopropylmethylamine (0.12 mL of a 0.2 M NMP solution containing 5% of N-methylmorpholine). The mixture is heated for 6 hours at 65° C. The reaction mixture is washed with 1N sodium hydroxide. The product is extracted in ethyl acetate then adsorbed on a silica gel based solid phase extraction (SPE) column (1 g) and eluted with a 10:1:1 mixture of ethyl acetate:methanol:triethylamine. The solvent is evaporated to give the title compound as a solid.

B. 4-(2-Dimethylamino-1-oxoethyl)amino-2-methyl-9-(2,4,6-trimethylphenyl)-9H-pyridino[2,3-b]indole To a toluene solution of the compound from Example 4A (0.1 mL of a 0.2 M solution) is added a 0.5 M toluene solution of AlH$_3$.NMe$_2$Et complex (0.2 mL). The heterogeneous mixture is left at room temperature under argon for 2 hours, then treated with a 1:1 mixture of methanol:ethyl acetate. The reaction mixture is poured onto an SPE column and eluted with a mixture of ethyl acetate:methanol:triethylamine (10:2:1). The solvent is evaporated to give the title product as a solid.

EXAMPLE 5 (METHOD D)

A. 4-Chloro-2-methyl-9-(2,4,6-trimethylphenyl)-9H-pyridino[2,3-b]indole

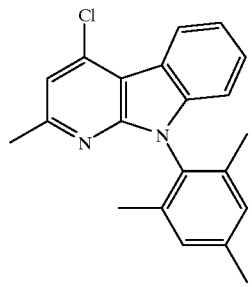

To an acetonitrile (10 mL) solution of tert-butylnitrite (0.65 g) is added copper (II) chloride (0.68 g). The compound from Example 1C (1.33 g) is added portionwise to the greenish-brown solution and the mixture is stirred for 12 hours. The acetonitrile is removed by evaporation and the residue is partitioned between water and dichloromethane. The aqueous layer is extracted with more dichloromethane and the combined extract is washed with water, dried over anhydrous sodium sulfate, filtered and concentrated. The product is filtered through a plug of silica gel using 20% ethyl acetate in hexanes as eluent to afford a tan colored solid: MS 335 (M+H).

B. 4-(2-(1-Methyl-2-pyrrolidino)ethyl)amino-2-methyl-9-(2,4,6-trimethylphenyl)-9H-pyridino[2,3-b]indole

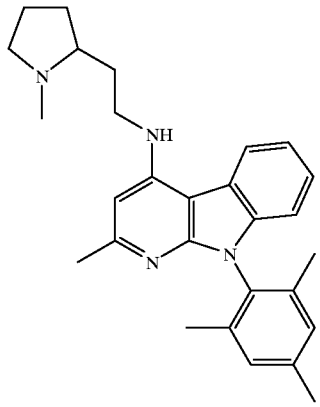

Combine the compound from Example 5A (200 mg) and 2-(2-aminoethyl)-1-methylpyrrolidine (1.0 mL) in N-methylpyrrolidinone (2 mL) and heat the solution to 120° C. for 12 hours. Pour mixture into water and extract with ethyl acetate. Wash extract with aqueous ammonium chloride then water. Dry extract over anhydrous sodium sulfate, filter and concentrate. Purify by preparative TLC using 10% methanol in dichloromethane as eluent: MS 427 (M+H).

EXAMPLE 6 (METHOD E)

A. 2-Amino-1-phenyl-1H-indole-3-carbonitrile

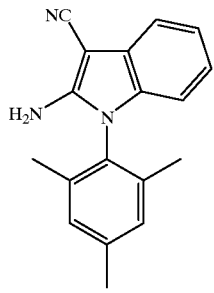

Dissolve the compound from Example 1A (20 g) in 1,4-dioxane (300 mL) and add DDQ (34 g) portionwise to the solution. The reaction is stirred for 1 hour then filtered through celite to remove insoluble side products. The filtrate is concentrated and allowed to solidify. The product is collected by filtration and washed with ethanol to yield 16 g of a tan colored powder: MS 276 (M+H).

B. 4-Hydroxy-2-methyl-9-(2,4,6-trimethylphenyl)-9H-pyrimidino[4,5-b]indole

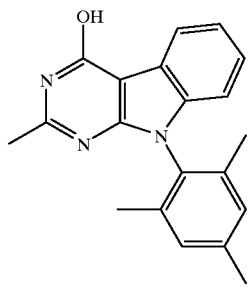

A mixture of the compound from Example 6A (30 g), acetic anhydride (15 mL) and acetic acid (30 mL) is refluxed for 1 hour then, concentrated to a solid. Phosphoric acid (40 mL, 85%) is added to the amide. The mixture is then refluxed for 0.5 hour and cooled to ambient temperature. The solution is poured onto ice and the precipitate that forms is collected by filtration. The solids are washed with water and some ethanol: MS 318 (M+H).

C. 4-Chloro-2-methyl-9-(2,4,6-trimethylphenyl)-9H-pyrimidino[4,5-b]indole

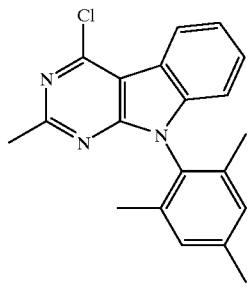

The compound from Example 6B (2.2 g) is refluxed in phosphoryl chloride (30 mL) for 3 hours. The excess phosphoryl chloride is removed under reduced pressure and the residue is partitioned between aqueous potassium carbonate and dichloromethane. The aqueous is extracted with more dichloromethane. The combined extracts are dried over sodium sulfate, filtered and concentrated to give a tan colored solid: MS 336 (M+H).

D. 4-(2-Aminoethyl)amino-2-methyl-9-(2,4,6-trimethylphenyl)-9H-pyrimidino[4,5-b]indole

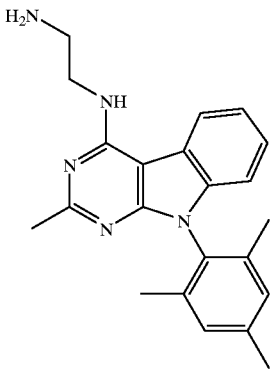

A mixture of the compound from Example 6C (750 mg) and ethylenediamine (1.0 mL) in N-methylpyrrolidinone (4 mL) is heated to 100° C. for 20 hours. Dilute mixture with ethyl acetate and wash with water and, brine, dry over sodium sulfate, filter and concentrate to give a tan colored solid. Purify by radial chromatography using 30% methanol and 0.5% ammonium hydroxide in dichloromethane as eluent: MS 360 (M+H).

EXAMPLE 7 (METHOD F)

4-(2-(Cyclohexylamino)ethyl)oxy-2-methyl-9-(2,4,6-trimethylphenyl)-9H-pyrimidino[4,5-b]indole

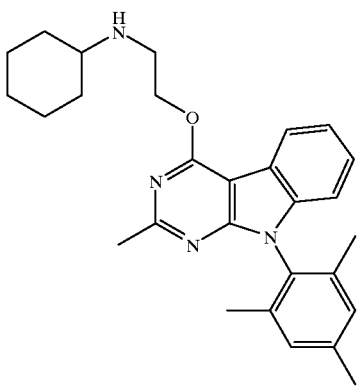

To a solution of the compound from Example 6C (100 mg) and N-cyclohexyl-ethanolamine (215 mg) in anhydrous tetrahydrofuran (1 mL) under nitrogen atmosphere with magnetic stirring is added 1M potassium tert-butoxide solution in tetrahydrofuran (0.5 mL). After 18 hours, the reaction mixture is partitioned between water (10 mL) and ethyl acetate (30 mL). The organic layer is separated, washed with saturated ammonium chloride solution (10 mL×2) and brine (10 mL), dried over anhydrous sodium sulfate, filtered, and evaporated at reduced pressure to obtain a viscous yellow oil. Purify by chromatography on silica gel eluting with 5% methanol and 0.5% ammonium hydroxide in dichloromethane to obtain a pale yellow oil: TLC (5% methanol/ 0.5% ammonium hydroxide/dichloromethane) Rf 0.30, MS 443 (M+H).

EXAMPLE 8 (METHOD G)

4-(2-(Cyclohexylamino)ethyl)amino-2-methyl-9-(2, 4,6-trimethylphenyl)-9H-pyrimidino[4,5-b]indole

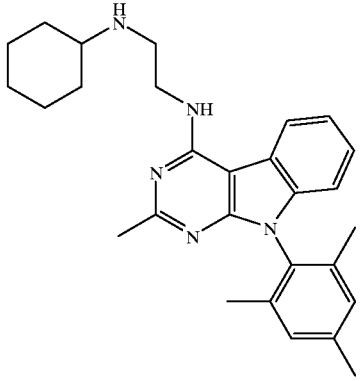

To a solution of the compound from Example 6D (100 mg) and cyclohexanone (54.6 mg) in anhydrous methanol (1.5 ML) under nitrogen atmosphere with magnetic stirring is added 3Å molecular sieves (200 mg) followed by 1 N HCl (28 μl). After 15 minutes, sodium cyanoborohydride (70 mg) is added and the reaction is stirred for 18 hours. The reaction mixture is filtered through celite, diluted with ethyl acetate (30 mL), washed with saturated ammonium chloride solution (10 mL), saturated sodium bicarbonate solution (10 mL), and brine (10 mL). The resulting colorless solution is dried over anhydrous sodium sulfate, filtered, and evaporated at reduced pressure to obtain a colorless oil. Purify by chromatography on silica gel eluting with 10% methanol and 0.5% ammonium hydroxide in dichloromethane to obtain a colorless oil: TLC (10% methanol/0.5% ammonium hydroxide/ dichloromethane) Rf 0.31, MS 442 (M+H).

EXAMPLE 9 (METHOD H)

4-(2-(2-Phenethylamino)ethyl)amino-2-methyl-9-(2, 4,6-trimethylphenyl)-9H-pyrimidino[4,5-b]indole

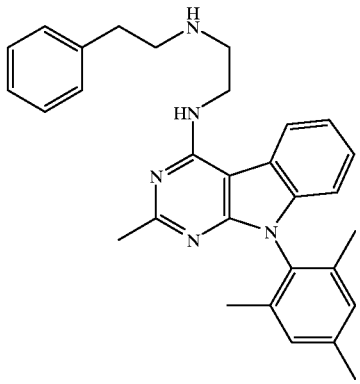

A two phase mixture of the compound from Example 6D (71 mg), phenethyl bromide (250 mg) in ethyl acetate (2 mL) and saturated aqueous sodium bicarbonate (1 mL) is heated to 60° C. for 24 hours. The mixture is diluted with ethyl acetate, washed with water, brine, dried over sodium sulfate, filtered and concentrated. Purify by radial chromatography using 10% methanol and 0.5% ammonium hydroxide in dichloromethane as eluent: TLC (10% methanol/0.5% ammonium hydroxide/dichloromethane) Rf 0.37, MS 464 (M+H).

EXAMPLE 10 (METHOD I)

A. 2-(3,4-dimethoxyphenyl)-N-(2-{[2-methyl-9-(2, 4,6-trimethylphenyl)pyrimidino[4,5-b]indol-4-yl] amino}ethyl)acetamide

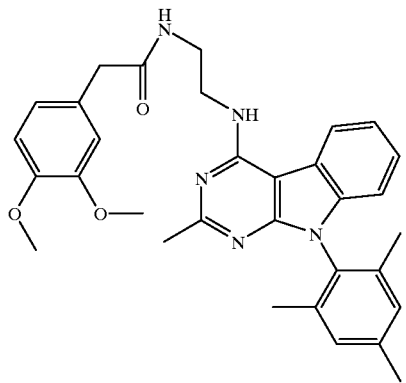

To a solution of the compound from Example 6D (300 mg) and 3,4-dimethoxyphenylacetic acid (164 mg) in anhydrous tetrahydrofuran (5 mL) under nitrogen atmosphere with magnetic stirring is added BOP reagent (369 mg) followed diisopropylethylamine (291 μl). After 18 h, the reaction mixture is evaporated at reduced pressure, diluted with ethyl acetate (60 mL), washed with saturated ammonium chloride solution (15 mL×2), saturated sodium bicarbonate solution (15 mL), brine (15 mL), dried over anhydrous sodium sulfate, filtered, and evaporated to obtain a yellow oil. Purify by radial chromatography using 5% methanol and 0.5% ammonium hydroxide in dichloromethane as eluent: TLC (5% methanol/0.5% ammonium hydroxide/ dichloromethane) Rf 0.42, MS 538 (M+H).

B. (2-{[2-(3,4-dimethoxyphenyl)ethyl]amino}ethyl)[2-methyl-9-(2,4,6-trimethylphenyl)pyrimidino[4,5-b]indol-4-yl]amine

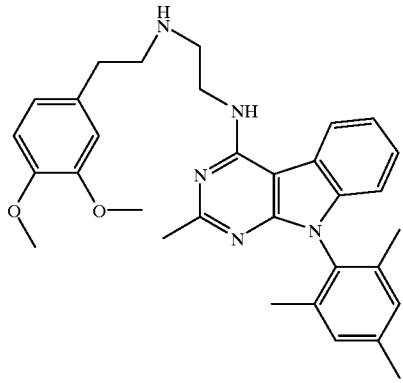

B. 4-(2-(Cyclopropylmethylamino)ethyl)amino-2-methyl-9-(2,4,6-trimethylphenyl)-9H-pyrimidino[4,5-b]indole

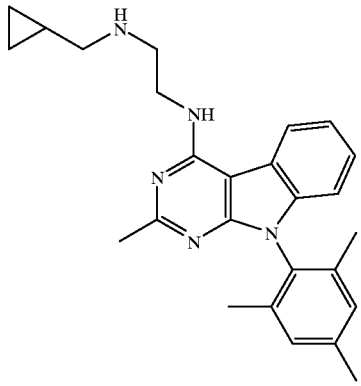

To a solution of 4-(2-(1-oxo-2-(3,4-dimethoxyphenyl) ethyl)ethyl)amino-2-methyl-9-(2,4,6-trimethylphenyl)-9H-pyrimidino [4,5-b]indole (440 mg) in anhydrous THF (15 mL) under nitrogen atmosphere with magnetic stirring is added 0.5 M $AlH_3 \cdot NMe_2Et$ complex in toluene (16.4 mL). The reaction mixture is heated at 50° C. for 2 hours, cooled to ambient temperature, and quenched by cautious addition of sodium carbonate decahydrate. The resulting mixture is diluted with ethyl acetate (60 mL), filtered through celite, and evaporated at reduced pressure to obtain a yellow oil. Purify by radial chromatography using 7% methanol and 0.5% ammonium hydroxide in dichloromethane as eluent: TLC (5% methanol/0.5% ammonium hydroxide/dichloromethane) Rf 0.07, MS 524 (M+H).

To a solution of the compound from Example 11A (250 mg) in dichloromethane (15 mL) at 0° C. is added triethylamine (134 mg) followed by addition of methanesulfonyl chloride (97 mg). After stirring for 1 hour, the reaction mixture is diluted with dichloromethane, washed with 5% aqueous sodium bicarbonate solution then water, dried over sodium sulfate, filtered and concentrated. The intermediate compound is dissolved in N-methylpyrrolidinone (10 mL) and anhydrous ammonia gas is bubbled through the solution for 20 minutes. The mixture is allowed to stir at room temperature in a closed vessel for 1 hour. It is then diluted with ethyl acetate, washed with water, brine, dried over sodium sulfate, filtered and concentrated. The compound is purified by radial chromatography using 5% methanol and 0.5% ammonium hydroxide in dichloromethane as eluent to give product that crystallizes on standing: MS 400 (M+H).

EXAMPLE 11 (METHOD J)

A. 4-(N-(2-hydroxyethyl)-N-cyclopropylmethyl) amino-2-methyl-9-(2,4,6-trimethylphenyl)-9H-pyrimidino[4,5-b]indole

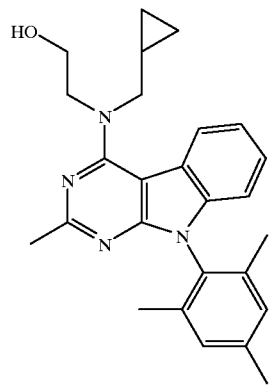

EXAMPLE 12 (METHOD K)

A. 4-(2-(1-Oxo-2-(3-methoxy-4-hydroxyphenyl) ethylamino) ethyl)amino-2-methyl-9-(2,4,6-trimethylphenyl)-9H-pyridino[2,3-b]indole

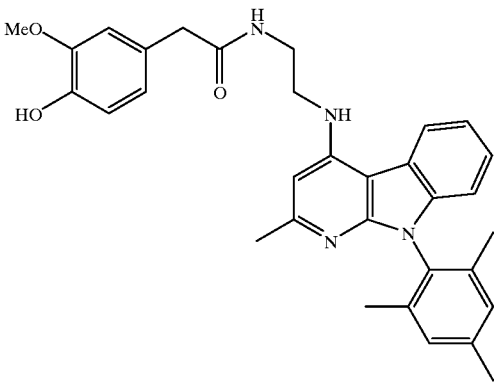

A solution of the compound from Example 6C (700 mg), N-cyclopropylmethyl-N-(2-hydroxyethyl)amine (960 mg) in N-methylpyrrolidinone is heated to 100° C. for 5 hours. Dilute with ethyl acetate, wash with water, brine, dry over sodium sulfate, filter and concentrate. Purify by radial chromatography using 50% ethyl acetate in hexanes as eluent: MS 415 (M+H).

A solution of the compound from Example 3 (0.600 g, 1.67 mmol) and 4-hydroxy-3-methoxyphenylacetic acid (0.3 g, 1.67 mmol) in dichloromethane (20 mL) is treated with BOP (0.815 g, 1.84 mmol) and N,N-diisopropylethyl amine (0.321 mL, 1.84 mmol). The mixture is stirred at room temperature for 3 hours. The resulting mixture is washed successively with dichloromethane (50 mL), water (50 mL), and saturated sodium chloride solution (50 mL). The organic portion is dried over anhydrous sodium sulfate, filtered and concentrated to give the phenol intermediate, alternatively named 2-(4-hydroxy-3-methoxyphenyl)-N-(2-{[2-methyl-9-(2,4,6-trimethylphenyl)-pyridino[2,3-b]indol-4-yl]amino}ethyl)acetamide, which is used without further purification (TLC Rf 0.50; elution with 5% methanol-dichloromethane).

B. 4-(2-(1-Oxo-2-(3-methoxy-4-propoxyphenyl)ethylamino) ethyl)amino-2-methyl-9-(2,4,6-trimethylphenyl)-9H-pyridino[2,3-b]indole

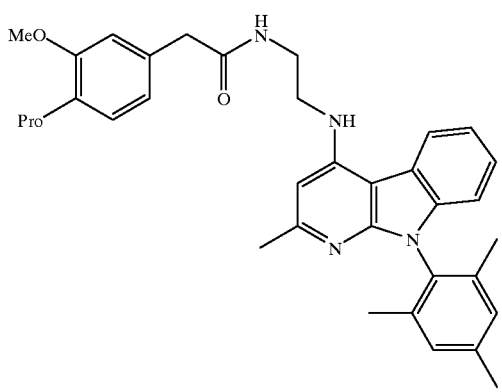

A solution of the compound from example 12A (0.050 g, 0.096 mmol) and propyl iodide (0.014 mL, 0.143 mmol) in acetone (5 mL) is treated with aqueous potassium carbonate (4M, 0.382 mmol) (Note: in cases where the alkylating reagent is insoluble, a phase transfer catalyst, such as tetrabutylammonium bromide, can be added to facilitate the reaction). The mixture is heated to reflux. After completion of the reaction (2–5 hours as indicated by TLC), the solution is cooled to room temperature, quenched with a saturated aqueous solution of ammonium chloride (5 mL), and extracted with ethyl acetate. The organic layer is separated, dried over anhydrous sodium sulfate, filtered and concentrated. Purification by preparative TLC, eluting with 5 % methanol-dichloromethane, affords the title compound, alternatively named 2-(3-methoxy-4-propoxyphenyl)-N-(2-{[2-methyl-9-(2,4,6-trimethylphenyl)-pyridino[2,3-b]indol-4-yl]amino}ethyl)acetamide, as a white solid (TLC Rf 0.35; elution 5% methanol-dichloromethane).

C. 4-(2-(2-(3-Methoxy-4-propoxyphenyl)ethylamino)ethyl)amino-2-methyl-9-(2,4,6-trimethylphenyl)-9H-pyridino[2,3-b]indole

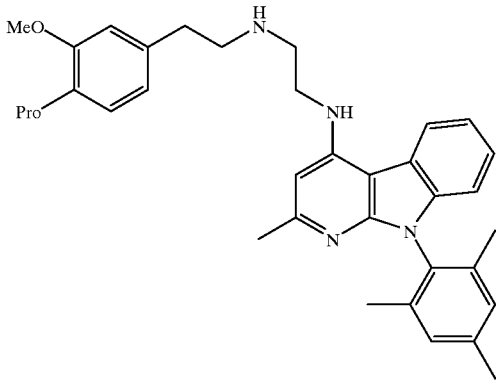

A solution of the compound from Example 12B (0.05 g, 0.088 mmol) in THF (3 mL) is treated with AlH$_3$.NMe$_2$Et (1.77 mL, 0.885 mmol). The mixture is heated to reflux for 8 hours. The resulting mixture is cooled to room temperature. Sodium carbonate (0.500 g) was added, and the mixture is stirred at room temperature for 15 min. The solution is filtered through Celite which is washed with several portions of dichloromethane. The filtrate is concentrated in vacuo to dryness, and the residue is purified by preparative TLC (10% methanol-dichloromethane) to give the title compound, alternatively named (2-{[2-(3-methoxy-4-propoxyphenyl)ethyl]-amino}ethyl)[2-methyl-9-(2,4,6-trimethylphenyl)pyridino[2,3-b]indol-4-yl]amine, as white solid (TLC Rf 0.28; elution with 10% methanol-dichloromethane).

EXAMPLE 13 (METHOD L)

A. 4-(2-(1-Oxo-2-(3-methoxy-4-cyclopentyloxyphenyl) ethylamino)ethyl)amino-2-methyl-9-(2,4,6-trimethylphenyl)-9H-pyridino[2,3-b]indole

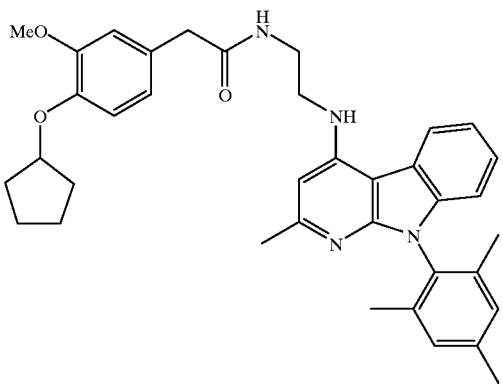

To a solution of the compound from example 12A (0.100 g, 0.191 mmol), cyclopentanol (0.026 mL, 0.287 mmol), and triphenyl phosphine (0.075 g, 0.287 mmol) in THF (8 mL) is added dropwise over 2 min diethylazodicarboxylate (0,050 g, 0.287 mmol). The mixture is heated to reflux for 3 hours. The resulting mixture is cooled to room temperature and concentrated to dryness. Purification by flash column chromatography (5% methanol-dichloromethane) to give the title compound as a yellow solid (TLC Rf 0.35; elution 5% methanol-dichloromethane).

B. 4-(2-(2-(3-Methoxy-4-cyclopentyloxphenyl) ethylamino)ethyl)amino-2-methyl-9-(2,4,6-trimethylphenyl)-9H-pyridino[2,3-b]indole

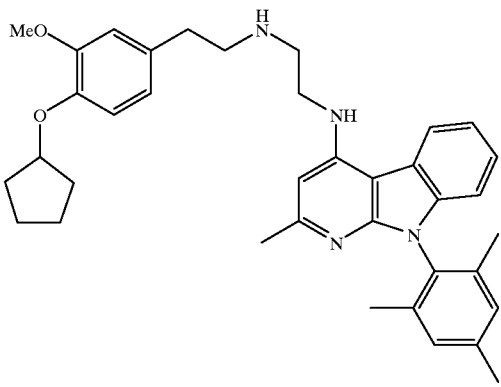

A solution of the compound from Example 13A (0.089 g, 0.151 mmol) in THF (5 mL) is treated with $AlH_3 \cdot NMe_2Et$ (3.00 mL, 1.507 mmol). The mixture is heated to reflux for 18 hours. The resulting mixture is cooled to room temperature. Sodium carbonate (1.00 g) is added, and stirred at room temperature for 15 min. The solution is filtered through Celite which is washed with several portions of dichloromethane. The filtrate is concentrated in vacuo to dryness and the residue purified by preparative TLC (10% methanol-dichloromethane) to give the title compound as a white solid.

Using the above procedures and modifications known to one skilled in the art of organic synthesis, the examples described in Table 1 may be prepared. Meanings for the abbreviations used are: Ex=example, Meth.=method of preparation (as described above), m/e=experimentally determined mass ion (M+1), Ph=phenyl, Me=methyl, Et=ethyl, Pr=propyl, iPr=isopropyl, cPr=cyclopropyl, Bu=butyl, iBu=isobutyl, tBu=tert-butyl, Pent=pentyl, cPent =cyclopentyl, Hex=hexyl, cHex=cyclohexyl, Hep=heptyl, cHep=cycloheptyl.

TABLE 1

The compounds of the following examples have the general formula shown below and contain the substituents listed in the table.

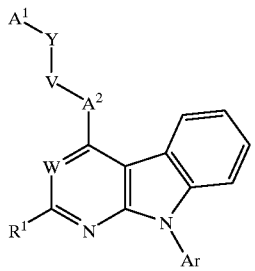

| Ex | W  | $A^2$ | V—Y—$A^1$                                    | Ar            | $R^1$ | m/e | Meth |
|----|----|-------|----------------------------------------------|---------------|-------|-----|------|
| 14 | N  | NH    | $(CH_2)_2$-(4-piperidyl)                     | 2,4,6-triMe—Ph | Me    | 428 | E    |
| 15 | N  | NH    | $(CH_2)_2$—NEt-imidazol-5-yl                 | 2,4,6-triMe—Ph | Me    | 468 | G    |
| 16 | CH | NH    | $(CH_2)_2$—NH-(1,1-diMe)—Pr                  | 2,4,6-triMe—Ph | Me    | 429 | C    |
| 17 | CH | NH    | $(CH_2)_2$—NH-(1,3-diMe)—Bu                  | 2,4,6-triMe—Ph | Me    | 443 | C    |
| 18 | CH | NH    | $(CH_2)_2$—NH-(2-Et)—Pr                      | 2,4,6-triMe—Ph | Me    | 429 | G    |
| 19 | CH | NH    | $(CH_2)_2$—NH-(2-Me)—Bu                      | 2,4,6-triMe—Ph | Me    | 429 | C    |
| 20 | CH | NH    | $(CH_2)_2$—NH-(2-Me)—Pr                      | 2,4,6-triMe—Ph | Me    | 415 | C    |
| 21 | CH | NH    | $(CH_2)_2$—NH-(2-Me)—Pr                      | 2,4,6-triMe—Ph | Me    | 415 | C    |
| 22 | CH | NH    | $(CH_2)_2$—NH-(3-Me)—Bu                      | 2,4-diMe—Ph    | Me    | 429 | C    |
| 23 | N  | NH    | $(CH_2)_2$—NH—(C=O)—$CH_2$-(3,4-di MeO—Ph)   | 2,4,6-triMe—Ph | Me    | 538 | I    |
| 24 | N  | NH    | $(CH_2)_2$—NH—(C=O)—$CH_2$-(4-MeO—Ph)        | 2,4,6-triMe—Ph | Me    | 508 | I    |
| 25 | N  | NH    | $(CH_2)_2$—NH—(C=O)-imidazol-5-yl            | 2,4,6-triMe—Ph | Me    | 454 | I    |
| 26 | N  | NH    | $(CH_2)_2$—NH—(C=O)-pyrazin-2-yl             | 2,4,6-triMe—Ph | Me    | 466 | I    |
| 27 | CH | NH    | $(CH_2)_2$—NH—$(CH_2)_2$-(2-MeO—Ph)          | 2,4,6-triMe—Ph | Me    | 493 | A    |
| 28 | CH | NH    | $(CH_2)_2$—NH—$(CH_2)_2$-(2,4-diMeO—Ph)      | 2,4,6-triMe—Ph | Me    | 523 | A    |
| 29 | CH | NH    | $(CH_2)_2$—NH—$(CH_2)_2$-(3-MeO-4-($OCH_2$-cPr)—Ph) | 2,4,6-triMe—Ph | Me    | 563 | K    |
| 30 | CH | NH    | $(CH_2)_2$—NH—$(CH_2)_2$-(3-MeO-4-cHexo-Ph)  | 2,4,6-triMe—Ph | Me    | 591 | L    |
| 31 | N  | NH    | $(CH_2)_2$—NH—$(CH_2)_2$-(3-MeO-4-EtO—Ph)    | 2,4,6-triMe—Ph | Me    | 538 | I    |
| 32 | CH | NH    | $(CH_2)_2$—NH—$(CH_2)_2$-(3-MeO-4-EtO—Ph)    | 2,4,6-triMe—Ph | Me    | 537 | A    |

TABLE 1-continued

The compounds of the following examples have the general formula shown below and contain the substituents listed in the table.

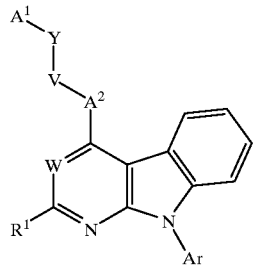

| Ex | W | A² | V—Y—A¹ | Ar | R¹ | m/e | Meth |
|---|---|---|---|---|---|---|---|
| 33 | CH | NH | (CH₂)₂—NH—(CH₂)₂-(3-MeO-4-iPrO—Ph) | 2,4,6-triMe—Ph | Me | 551 | K |
| 34 | CH | NH | (CH₂)₂—NH—(CH₂)₂-(3-MeO-4-BuO—Ph) | 2,4,6-triMe—Ph | Me | 565 | K |
| 35 | CH | NH | (CH₂)₂—NH—(CH₂)₂-(3-MeO-4-O((2-Me)—Pr)—Ph) | 2,4,6-triMe—Ph | Me | 565 | A |
| 36 | CH | NH | (CH₂)₂—NH—(CH₂)₂-(3-MeO-4-OH—Ph) | 2,4,6-triMe—Ph | Me | 509 | A |
| 37 | CH | NH | (CH₂)₂—NH—(CH₂)₂-(3-MeO-4-PentO—Ph) | 2,4,6-triMe—Ph | Me | 579 | K |
| 38 | CH | NH | (CH₂)₂—NH—(CH₂)₂-(3,4-diMeO—Ph) | 2,4,6-triMe—Ph | Me | 523 | A |
| 39 | CH | NH | (CH₂)₂—NH—(CH₂)₂-(3,4-diMeO—Ph) | 2,6-diMe—Ph | Me | 509 | C |
| 40 | N | NH | (CH₂)₂—NH—(CH₂)₂-(4-CF₃—Ph) | 2,4,6-triMe—Ph | Me | 532 | I |
| 41 | N | NH | (CH₂)₂—NH—(CH₂)₂-(4-EtO—Ph) | 2,4,6-triMe—Ph | Me | 508 | I |
| 42 | CH | NH | (CH₂)₂—NH—(CH₂)₂-(4-EtO—Ph) | 2,4,6-triMe—Ph | Me | 507 | C |
| 43 | N | NH | (CH₂)₂—NH—(CH₂)₂-(4-MeO—Ph) | 2,4,6-triMe—Ph | Me | 494 | I |
| 44 | CH | NH | (CH₂)₂—NH—(CH₂)₂-(4-MeO—Ph) | 3,5-diMe—Ph | Me | 479 | I |
| 45 | CH | NH | (CH₂)₂—NH—(CH₂)₂-(4-NH₂—Ph) | 2,4,6-triMe—Ph | Me | 478 | A |
| 46 | CH | NH | (CH₂)₂—NH—(CH₂)₂-(4-OH—Ph) | 2,4,6-triMe—Ph | Me | 479 | A |
| 47 | N | NH | (CH₂)₂—NH—(CH₂)₂-imidazol-5-yl | 2,4,6-triMe—Ph | Me | 454 | I |
| 48 | CH | NH | (CH₂)₂—NH—(CH₂)₂-imidazol-5-yl | 2,4,6-triMe—Ph | Me | 453 | A |
| 49 | CH | NH | (CH₂)₂—NH—(CH₂)₂-morpholin-4-yl | 2,4,6-triMe—Ph | Me | 472 | A |
| 50 | CH | NH | (CH₂)₂—NH—(CH₂)₂—Ph | 2,4,6-triMe—Ph | Me | 463 | A |
| 51 | N | NH | (CH₂)₂—NH—(CH₂)₂—Ph | 2,4,6-triMe—Ph | Me | 464 | E |
| 52 | CH | NH | (CH₂)₂—NH—(CH₂)₂-pyridin-2-yl | 2,4,6-triMe—Ph | Me | 464 | A |
| 53 | CH | NH | (CH₂)₂—NH—(CH₂)₂-pyridin-3-yl | 2,4,6-triMe—Ph | Me | 464 | A |
| 54 | CH | NH | (CH₂)₂—NH—(CH₂)₂-pyridin-4-yl | 2,4,6-triMe—Ph | Me | 464 | A |
| 55 | CH | NH | (CH₂)₂—NH—(CH₂)₃—Ph | 2,4,6-triMe—Ph | Me | 476 | A |
| 56 | CH | NH | (CH₂)₂—NH—(CH₂)₄—Ph | 2,4,6-triMe—Ph | Me | 491 | A |
| 57 | N | NH | (CH₂)₂—NH—(CO)—CH₂-imidazol-5-yl | 2,4,6-triMe—Ph | Me | 468 | I |
| 58 | N | NH | (CH₂)₂—NH—(CO)-cPr | 2,4,6-triMe—Ph | Me | 428 | I |
| 59 | CH | NH | (CH₂)₂—NH—Bu | 2,4,6-triMe—Ph | Me | 429 | C |
| 60 | CH | NH | (CH₂)₂—NH—Bu | 2,4,6-triMe—Ph | Me | 415 | C |
| 61 | N | NH | (CH₂)₂—NH-cBu | 2,4,6-triMe—Ph | Me | 414 | G |
| 62 | CH | NH | (CH₂)₂—NH-cBu | 2,4,6-triMe—Ph | Me | 413 | A |
| 63 | N | NH | (CH₂)₂—NH—CH₂-(2-Me-imidazol-4-yl) | 2,4,6-triMe—Ph | Me | 454 | G |
| 64 | CH | NH | (CH₂)₂—NH—CH₂-(3-MeO—Ph) | 2,4,6-triMe—Ph | Me | 479 | A |
| 65 | CH | NH | (CH₂)₂—NH—CH₂-(4-EtO—Ph) | 2,4,6-triMe—Ph | Me | 493 | A |
| 66 | CH | NH | (CH₂)₂—NH—CH₂-(4-MeO—Ph) | 2,4,6-triMe—Ph | Me | 479 | A |
| 67 | N | O | (CH₂)₂—NH—CH₂-cPr | 2,4,6-triMe—Ph | Me | 415 | F |
| 68 | CH | NH | (CH₂)₂—NH—CH₂-cPr | 2,4,6-triMe—Ph | Me | 413 | A |
| 69 | N | NH | (CH₂)₂—NH—CH₂-imidazol-5-yl | 2,4,6-triMe—Ph | Me | 440 | I |
| 70 | N | NH | (CH₂)₂—NH-cHex | 2,4,6-triMe—Ph | Me | 442 | G |
| 71 | CH | NH | (CH₂)₂—NH-cHex | 2,4,6-triMe—Ph | Me | 441 | A |
| 72 | CH | NH | (CH₂)₂—NH-cHex | 3,5-diMe—Ph | Me | 427 | A |
| 73 | CH | NH | (CH₂)₂—NH-cHex | 2,4-diMe—Ph | Me | 427 | C |
| 74 | N | NH | (CH₂)₂—NH-cPent | 2,4,6-triMe—Ph | Me | 428 | G |
| 75 | CH | NH | (CH₂)₂—NH-cPent | 2,4,6-triMe—Ph | Me | 427 | A |
| 76 | CH | NH | (CH₂)₂—NH-cPent | 3,5-diMe—Ph | Me | 413 | A |
| 77 | N | NH | (CH₂)₂—NH-cPent | 2,4,6-triMe—Ph | Et | 442 | A |
| 78 | CH | NH | (CH₂)₂—NH-cPent | 2,4-diMe—Ph | Me | 413 | C |
| 79 | N | NH | (CH₂)₂—NH-aPr | 2,4,6-triMe—Ph | Me | 400 | I |
| 80 | CH | NH | (CH₂)₂—NH—Et | 2,4,6-triMe—Ph | Me | 387 | A |
| 81 | N | NH | (CH₂)₂—NH—Et | 2,4,6-triMe—Ph | Me | 388 | E |
| 82 | N | NH | (CH₂)₂—NH—Et | 2-Me-4-MeO—Ph | Me | 390 | E |
| 83 | N | NH | (CH₂)₂—NH—Et | 2-Me-4-Cl—Ph | Me | 394 | E |
| 84 | CH | NH | (CH₂)₂—NH-Hex | 2,4,6-triMe—Ph | Me | 443 | C |
| 85 | N | NH | (CH₂)₂—NH-iPr | 2,4,6-triMe—Ph | Me | 402 | E |
| 86 | CH | NH | (CH₂)₂—NH-iPr | 2,4,6-triMe—Ph | Me | 401 | C |
| 87 | N | NH | (CH₂)₂—NH—Me | 2,4,6-triMe—Ph | Me | 374 | E |
| 88 | CH | NH | (CH₂)₂—NH—Me | 2,4,6-triMe—Ph | Me | 373 | A |
| 89 | N | NH | (CH₂)₂—NH—Pr | 2,4,6-triMe—Ph | Me | 402 | E |
| 90 | CH | NH | (CH₂)₂—NH—Pr | 2,4,6-triMe—Ph | Me | 401 | C |
| 91 | N | O | (CH₂)₂—NH-tBu | 2,4,6-triMe—Ph | Me | 417 | F |
| 92 | CH | NH | (CH₂)₂—NH-tBu | 2,4,6-triMe—Ph | Me | 415 | C |

TABLE 1-continued

The compounds of the following examples have the general formula shown below and contain the substituents listed in the table.

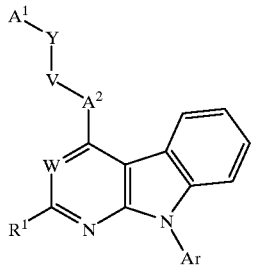

| Ex | W | A² | V—Y—A¹ | Ar | R¹ | m/e | Meth |
|---|---|---|---|---|---|---|---|
| 93 | N | NH | (CH₂)₂—NH₂ | 2,4,6-triMe—Ph | Et | 374 | E |
| 94 | N | NH | (CH₂)₂—NH₂ | 2,4,6-triMe—Ph | CF3 | 414 | E |
| 95 | N | NH | (CH₂)₂—NH₂ | 2-Me-4-MeO—Ph | Me | 362 | E |
| 96 | CH | NH | (CH₂)₂—NMe-cPent | 2,4,6-triMe—Ph | Me | 441 | K |
| 97 | N | NH | (CH₂)₂—NMe₂ | 2,4,6-triMe—Ph | Me | 388 | E |
| 98 | N | NH | (CH₂)₂-pyrrolidinyl | 2,4,6-triMe—Ph | Me | 414 | E |
| 99 | N | NH | (CH₂)₃-(piperidin-4-yl) | 2,4,6-triMe—Ph | Me | 442 | E |
| 100 | N | NH | (CH₂)₃—NH—(CH₂)₂-morpholin-4-yl | 2,4,6-triMe—Ph | Me | 444 | E |
| 101 | N | NH | (CH₂)₃—NH₂ | 2,4,6-triMe—Ph | Me | 374 | E |
| 102 | N | O | (CH₂)₃-piperidinyl | 2,4,6-triMe—Ph | Me | 443 | F |
| 103 | N | NH | (CH₂)₃-pyrrolidinyl | 2,4,6-triMe—Ph | Me | 428 | E |
| 104 | N | NH | (CH₂)₄—NH₂ | 2,4,6-triMe—Ph | Me | 388 | E |
| 105 | N | NH | CH₂—(C═O)—NH₂ | 2,4,6-triMe—Ph | Me | 374 | E |
| 106 | N | NH | CH₂—(S)-(pyrrolidin-2-yl) | 2,4,6-triMe—Ph | Me | 400 | E |
| 107 | N | NH | CH₂—CHMe—NH-cPent | 2,4,6-triMe—Ph | Me | 442 | G |
| 108 | N | NH | CH₂—CHMe—NH₂ | 2,4,6-triMe—Ph | Me | 374 | E |
| 109 | N | NH | CH₂—CMe₂—NH—(CH₂)₂-((3-MeO-4-EtO)—Ph) | 2,4,6-triMe—Ph | Me | 566 | I |
| 110 | N | NH | CH₂—CMe₂—NH-cPent | 2,4,6-triMe—Ph | Me | 456 | G |
| 111 | N | NH | CH₂—CMe₂—NH-cPr | 2,4,6-triMe—Ph | Me | 442 | G |
| 112 | N | NH | CH₂—CMe₂—NH₂ | 2,4,6-triMe—Ph | Me | 388 | E |
| 113 | N | NH | cis-2-amino-cyclohexyl | 2,4,6-triMe—Ph | Me | 414 | E |
| 114 | CH | NH | (CH₂)₂—NH—CH₂-(4-NMe₂—Ph) | 2,4,6-triMe—Ph | Me | 492 | A |
| 115 | N | NH | (CH₂)₂—NH-cHep | 2,4,6-triMe—Ph | Me | 456 | F |
| 116 | N | NH | (CH₂)₂—NH—CH₂—(2-Me-(1,3-thiazol)-4-yl) | 2,4,6-triMe—Ph | Me | 471 | H |
| 117 | N | NH | (CH₂)₂—NH—CH₂-(5-Br-2-Me-(1,3-thiazol-4-yl) | 2,4,6-triMe—Ph | Me | 550 | H |
| 118 | CH | NH | (CH₂)₂—NH—CH₂—(C═O)-(2H,3H-benzo[e]1,4-dioxin-6-yl) | 2,4,6-triMe—Ph | Me | 535 | A |
| 119 | CH | NH | (CH₂)₂—NH—(CH₂)₂-(2H,3H-benzo[e]1,4-dioxin-6-yl) | 2,4,6-triMe—Ph | Me | 521 | A |
| 120 | CH | NH | (CH₂)₂—NH—(CH₂)₂-(2H-benzo[3,4-d]1,3-dioxolan-5-yl) | 2,4,6-triMe—Ph | Me | 507 | A |
| 121 | CH | NH | (CH₂)₂—NH-cHep | 2,4,6-triMe—Ph | Me | 455 | C |
| 122 | CH | NH | CH₂—(C═O)—NH—(CH₂)₂-(3,4-diMeO—Ph) | 2,4,6-triMe—Ph | Me | 537 | M |

The pharmaceutical utility of compounds of this invention are indicated by the following assays for human NPY-1 receptor activity.

Assay for Human NPY-1 Receptor Binding Activity

Compounds are assayed for activity using the following method: Baculovirus-infected Sf9 cells expressing recombinant human NPY-1 receptors are harvested at 42–48 hours at which time batches of 500 mL of cell suspension are pelleted by centrifugation. Each pellet is re-suspended in 30 mL of lysis buffer (10 mM HEPES, 250 mM sucrose, 0.5 μg/mL leupeptin, 2 μ/mL Aprotonin, 200 μM PMSF and 2.5 mM EDTA, pH 7.4) and gently homogenized by 50 strokes using a dounce homogenizer. The homogenate is centrifuged at 4° C. for 10 minutes at 536×g to pellet the nuclei. The supernatant is collected into a fresh tube and centrifuged twice in the same buffer at 48,000×g for 40 minutes. The final pellet was re-suspended in 10 mL of PBS containing 5 mM EDTA by dounce homogenization and stored in aliquots at −80° C.

Purified membranes are washed by PBS and re-suspended by gentle pipetting in binding buffer (50 mM Tris(HCl), 5 mM KCl, 120 mM NaCl, 2 mM CaCl₂, 1 mM MgCl₂, 0.1% bovine serum albumin (BSA), pH 7.4). Membranes (5 μg) are added to siliconized (Sigmacote, Sigma) polypropylene tubes in addition to 0.050 nM [$^{125}$I]NPY(porcine) for competition analysis or 0.010–0.500 nM [$^{125}$I]NPY(porcine) for saturation analysis. For evaluation of guanine nucleotide effects on receptor affinity, GTP is added at a final concentration of 100 μM. Cold displacers are added at concentrations ranging from $10^{-12}$ M to 10−6 M to yield a final volume of 0.250 mL. Nonspecific binding is determined in the presence of 1 μM NPY (human) and accounts for less than 10% of total binding. Following a 2 hour incubation at room temperature, the reaction is terminated by rapid vacuum filtration. Samples are filtered over presoaked GF/C Whatman filters (1.0% polyethyleneimine for 2 hours) and rinsed 2 times with 5 mL cold binding buffer lacking BSA. Remaining bound radioactivity is measured by gamma counting. To estimate the Bmax, Kd and Ki, the results of binding experiments are analyzed using SigmaPlot software (Jandel). The binding affinity for the compounds of the invention, expressed as an $IC_{50}$ value, generally range from about 0.5 nanomolar to about 10 micromolar.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

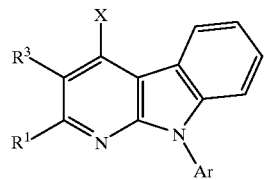

or a pharmaceutically acceptable salt thereof wherein:

Ar is phenyl, 1- or 2-naphthyl, 2-, 3-, or 4-pyridyl, 2-, 4- or 5-pyrimidinyl, each of which is optionally mono-, di-, or trisubstituted with halogen, trifluoromethyl, hydroxy, amino, $C_1$–$C_6$ alkylamino, di $C_1$–$C_6$ alkylamino, $C_3$–$C_7$ cycloalkylamino, carboxamido, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, $C_3$–$C_7$ cycloalkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, ($C_3$–$C_7$ cycloalkyl) $C_1$–$C_6$ alkyl, $C_3$–$C_7$ cycloalkyl, or ($C_1$–$C_6$ alkylene)—$G^1$—$R^2$ wherein $G^1$ is oxygen or sulfur and $R^2$ is hydrogen, $C_1$–$C_6$ alkyl, or $C_3$–$C_7$ cycloalkyl;

$R^3$ is hydrogen or $C_1$–$C_6$ alkyl;

x is

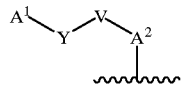

wherein $A^1$ is $NR^4R^5$ wherein $R^4$ and $R^5$ are independently:

hydrogen, a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl;

$C_1$–$C_6$ alkanoyl, ($C_3$–$C_7$ cycloalkyl) $C_1$–$C_6$ alkanoyl, $C_3$–$C_7$ cycloalkanoyl, $C_1$–$C_6$ alkylsulfonyl, or $C_3$–$C_7$ cycloalkylsulfonyl with the proviso that $R^4$ and $R^5$ may not both be alkanoyl or alkylsulfonyl;

$C_1$–$C_6$ heterocycloalkyl, wherein heterocycloalkyl is morpholinyl, piperazinyl, piperidinyl, or pyrrolidinyl; or aryl $C_1$–$C_6$ alkyl or heteroaryl $C_1$–$C_6$ alkyl, where aryl is phenyl, and heteroaryl is 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, di $C_1$–$C_6$ alkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where any 2 adjacent substituents may together form a 5–7 membered fused cycloalkyl or heterocycloalkyl ring; or $NR^4R^5$ taken together form a $C_3$–$C_6$ heterocycloalkyl, or a group of the formula:

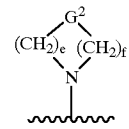

wherein e and f are independently 1, 2, or 3 and the sum of e and f is at least 3; and $G^2$ is
(i) $NR^6$ wherein $R^6$ is hydrogen, $C_1$–$C_6$ alkyl, ($C_3$–$C_7$ cycloalkyl) $C_1$–$C_6$ alkyl, or $C_3$–$C_7$ cycloalkyl; or
(ii) $CH(C_0$–$C_6$ alkyl)—$G^3$—$R^7$ wherein $G^3$ is —CONH—, —CONH($C_1$–$C_6$ alkyl)—, —NH—, —NH($C_1$–$C_6$ alkyl)—, —NH($C_3$–$C_7$ cycloalkyl)—, and $R^7$ is hydrogen, $C_1$–$C_6$ alkyl, ($C_3$–$C_7$ cycloalkyl) $C_1$–$C_6$ alkyl, or $C_3$–$C_7$ cycloalkyl; or
(iii) —$CONH_2$—, or —CO— wherein $R^8$ is hydrogen, $C_1$–$C_6$ alkyl, ($C_3$–$C_7$ cycloalkyl) $C_1$–$C_6$ alkyl, or $C_3$–$C_7$ cycloalkyl;

$A^2$ is NH, $SO_2$, oxygen or sulfur;

V is $CH_2$, CO, CS, $SO_2$, $CH(C_1$–$C_6$ alkyl), $CH(C_3$–$C_7$ cycloalkyl), with the proviso that V may not be CO, CS or $SO_2$ when A is $SO_2$, oxygen or sulfur; and Y is a bond or $C_1$–$C_6$ alkylene.

2. A compound according to claim 1 wherein $R^3$ is hydrogen, $A^2$ is NH or O, and $R^1$ is $C_1$–$C_6$ alkyl.

3. A compound according to claim 1 wherein $R^3$ is hydrogen, $R^4$ and $R^5$ are independently hydrogen, a $C_1$–$C_6$ alkyl group which optionally forms a heterocycloalkyl group with Y, ($C_3$–$C_7$ cycloalkyl) $C_1$–$C_6$ alkyl, or $C_3$–$C_7$ cycloalkyl.

4. A compound according to claim Ar is 2,4,6-trimethylphenyl, $A^2$ is NH or O, Y is $CH_2$, V is $CH_2$ or $(CH_2)_2$, $R^4$ is hydrogen, and $R^5$ is hydrogen, methyl, ethyl, propyl, isopropyl, 2-methylpropyl, 2-ethylpropyl, 1,1-dimethyl propyl, butyl, tert-butyl, 2-methylbutyl, 3-methylbutyl, 1,3-dimethyl butyl, hexyl, cyclopropyl, cyclobutyl, cyclopentyl, cyclohexyl, cycloheptyl, or cyclopropylmethyl.

5. A compound according to claim 1 wherein $R^3$ is hydrogen, Ar is 2,4,6-trimethylphenyl, $A^2$ is NH or O, Y is $CH_2$, V is $CH_2$ or $(CH_2)_2$, $R^4$ is hydrogen, and $R^5$ is $C_1$–$C_6$ heterocycloalkyl, wherein heterocycloalkyl is morpholin-4-yl, piperazin-4-yl, piperidin-4-yl, or pyrrolidin-2-yl.

6. A compound according to claim 1 wherein $R^3$ is hydrogen, Ar is 2,4,6-trimethylphenyl, $A^2$ is NH or O, Y is $CH_2$, V is $CH_2$ or $(CH_2)_2$, and $NR^4R^5$ taken together form a $C_3$–$C_6$ heterocycloalkyl, or a group of the formula:

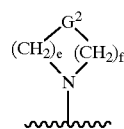

wherein e and f are independently 1, 2, or 3 and the sum of e and f is at least 3; and G² is (i) NR⁶ wherein R⁶ is hydrogen, $C_1$–$C_6$ alkyl, ($C_3$–$C_7$ cycloalkyl) $C_1$–$C_6$ alkyl, or $C_3$–$C_7$ cycloalkyl; or (ii) CH($C_0$—$C_6$ alkyl)—G³—R⁷ wherein G³ is —CONH—, —CONH($C_1$–$C_6$ alkyl)—, —NH—, —NH($C_1$–$C_6$ alkyl)—, —NH($C_3$–$C_7$ cycloalkyl)—, and R⁷ is hydrogen, $C_1$–$C_6$ alkyl, ($C_3$–$C_7$ cycloalkyl) $C_1$–$C_6$ alkyl, $C_3$–$C_7$ cycloalkyl; or (iii) —CONH₂—, or —CO[N($C_1$–$C_6$ alkylene)R⁸]— wherein R⁸ is hydrogen, $C_1$–$C_6$ alkyl, ($C_3$–$C_7$ cycloalkyl) $C_1$–$C_6$ alkyl, or $C_3$–$C_7$ cycloalkyl.

7. A compound according to claim 6 wherein NR⁴R⁵ is pyrrolidinyl, piperidinyl, morpholinyl, piperazinyl, N-methylpiperazinyl.

8. A compound according to claim 1 wherein R³ is hydrogen, R⁴ and R⁵ are independently hydrogen, aryl $C_1$–$C_6$ alkyl or heteroaryl $C_1$–$C_6$ alkyl, where aryl is phenyl, and heteroaryl is 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, $C_1$–$C_6$ alkylamino, di $C_1$–$C_6$ alkylamino, $C_3$–$C_7$ cycloalkylamino, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, or $C_3$–$C_7$ cycloalkoxy, where any 2 adjacent substituents may together form a 5–7 membered fused cycloalkyl or heterocycloalkyl ring.

9. A compound according to claim 8 wherein Ar is 2,4,6-trimethylphenyl, A² is NH or O, Y is CH₂, V is CH₂ or (CH₂)₂, R⁴ is hydrogen, and R⁵ is (CH₂)₂-phenyl, (CH₂)₃-phenyl, (CH₂)₄-phenyl, (CH₂)₂-(2-methoxy) phenyl, (CH₂)₂-(3-methoxy) phenyl, (CH₂)₂-(4-hydroxy) phenyl, (CH₂)₂-(4-methoxy) phenyl, (CH₂)₂-(4-ethoxy) phenyl, (CH₂)₂-(3-methoxy-4-ethoxy) phenyl, (CH₂)₂-(3-methoxy-4-isopropoxy) phenyl, (CH₂)₂-(3-methoxy-4-isobutyloxy) phenyl, (CH₂)₂-(3-methoxy-4-cyclopropylmethyloxy) phenyl, (CH₂)₂-(2,4-dimethoxy) phenyl, (CH₂)₂-(3,4-dimethoxy) phenyl, (CH₂)₂-(3-methoxy-4-hydroxy) phenyl, (CH₂)₂-(3-methoxy-4-propoxy) phenyl, (CH₂)₂-(3-methoxy-4-propoxy) phenyl, (CH₂)₂-(3-methoxy-4-butoxy) phenyl, (CH₂)₂-(3-methoxy-4-pentoxy) phenyl, (CH₂)₂-(3-methoxy-4-cyclopentyloxy) phenyl, (CH₂)₂-(3-methoxy-4-cyclohexyloxy) phenyl, (CH₂)₂-(2H-benzo[3,4-d]1,3-dioxolan-5-yl), (CH₂)₂-(2H,3H-benzo[e]1,4-dioxin-6-yl), (CH₂)₂-(4-trifluoromethyl) phenyl, (CH₂)₂-(4-amino) phenyl, or (CH₂)₂-(4-dimethylamino) phenyl.

10. A compound according to claim 8 wherein Ar is 2,4,6-trimethylphenyl, A² is NH or O, Y is CH₂, V is CH₂ or (CH₂)₂, R⁴ is hydrogen, and R⁵ is (CH₂)₂-(2-methylimidazol-4-yl), CH₂-imidazol-5-yl, or (CH₂)₂-(imidazol-5-yl).

11. A compound of the formula:

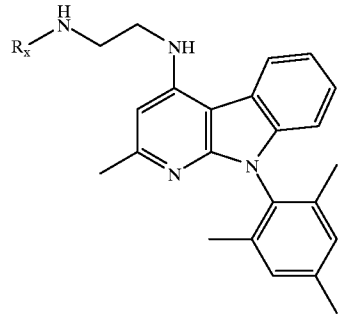

where $R_x$ is 1,1-dimethylpropyl; 1,3-dimethylbutyl; 2-ethylpropyl; 2-methylbutyl; 2-methylpropyl; 3-methylbutyl; 2-(2-methoxyphenyl)ethyl; 2-(2,4-dimethoxyphenyl)ethyl; 2-(3-methoxy-4-(cyclopropylmethoxy)phenyl)ethyl; 2-(3-methoxy-4-cyclohexyloxyphenyl)ethyl; 2-(3-methoxy-4-ethoxyphenyl)ethyl; 2-(3-methoxy-4-isopropoxyphenyl)ethyl; 2-(3-methoxy-4-butoxyphenyl)ethyl; 2-(3-methoxy-4-(2-methylpropoxy)phenyl)ethyl; 2-(3-methoxy-4-hydroxyphenyl)ethyl; 2-(3-methoxy-4-pentoxyphenyl)ethyl; 2-(3,4-dimethoxyphenyl)ethyl; 2-(4-ethoxyphenyl)ethyl; 2-(4-methoxyphenyl)ethyl; 2-(4-aminophenyl)ethyl; 2-(4-hydroxyphenyl)ethyl; 2-(imidazol-5-yl)ethyl; 2-(morpholin-4-yl)ethyl; 2-phenylethyl; 2-(2-pyridyl)ethyl; 2-(3-pyridyl)ethyl; 2-(4-pyridyl)ethyl; 3-phenylpropyl; 4-phenylbutyl; butyl; cyclobutyl; 3-methoxybenzyl; 4-ethoxybenzyl; 4-methoxybenzyl; cyclopropylmethyl; cyclohexyl; cyclopentyl; ethyl; hexyl; isopropyl; methyl; propyl; tertbutyl; 4-(dimethylamino)phenylmethyl; (2H,3H-benzo[e]1,4-dioxin-6-yl)carbonylmethyl; 2-((2H,3H-benzo[e]1,4-dioxin-6-yl)carbonyl)ethyl; or 2-(2H-benzo[3,4-d]1,3-dioxolan-5-yl)ethyl; cycloheptyl; 2-(3,4-dimethoxyphenyl)ethyl.

12. A compound according to claim 1, which is 4-(2-(2-(4-Methoxyphenyl)ethylamino)ethyl)amino-2-methyl-9-(2,4,6-trimethylphenyl)-9H-pyridino[2,3-b]indole.

13. A compound according to claim 1, which is 4-(2-Amino-2-methylethyl)amino-2-methyl-9-(2,4,6-trimethylphenyl)-9H-pyridino[2,3-b]indole.

14. A compound according to claim 1, which is 4-(2-Aminoethyl)amino-2-methyl-9-(2,4,6-trimethylphenyl)-9H-pyridino[2,3-b]indole.

15. A compound according to claim 1, which is 4-(2-Dimethylamino-1-oxoethyl)amino-2-methyl-9-(2,4,6-trimethylphenyl)-9H-pyridino[2,3-b]indole.

16. A compound according to claim 1, which is 4-(2-(1-Methyl-2-pyrrolidino)ethyl)amino-2-methyl-9-(2,4,6-trimethylphenyl)-9H-pyridino[2,3-b]indole.

17. A compound according to claim 1, which is 4-(2-(1-Oxo-2-(3-methoxy-4-hydroxyphenyl)ethylamino) ethyl)amino-2-methyl-9-(2,4,6-trimethylphenyl)-9H-pyridino[2,3-b]indole.

18. A compound according to claim 1, which is 4-(2-(1-Oxo-2-(3-methoxy-4-propoxyphenyl)ethylamino) ethyl)amino-2-methyl-9-(2,4,6-trimethylphenyl)-9H-pyridino[2,3-b]indole.

19. A compound according to claim 1, which is 4-(2-(2-(3-Methoxy-4-propoxyphenyl)ethylamino) ethyl)amino-2-methyl-9-(2,4,6-trimethylphenyl)-9H-pyridino[2,3-b]indole.

20. A compound according to claim 1, which is 4-(2-(1-Oxo-2-(3-methoxy-4-cyclopentyloxyphenyl) ethylamino)

ethyl)amino-2-methyl-9-(2,4,6-trimethylphenyl)-9H-pyridino[2,3-b]indole.

21. A compound according to claim 1, which is 4-(2-(2-(3-Methoxy-4-cyclopentyloxyphenyl)ethylamino) ethyl)amino-2-methyl-9-(2,4,6-trimethylphenyl)-9H-pyridino[2,3-b]indole.

22. A compound according to claim 1, which is (2-{[2-(3,4-dimethoxyphenyl)ethyl]amino}ethyl)[9-(2,6-dimethylphenyl)-2-methylpyridino[2,3-b]indol-4-yl]amine.

23. A compound according to claim 1, which is [9-(3,5-dimethylphenyl)-2-methylpyridino[2,3-b]indol-4-yl](2-{[2-(4-methoxyphenyl)ethyl]amino}ethyl)amine.

24. A compound according to claim 1, which is [9-(3,5-dimethylphenyl)-2-methylpyridino[2,3-b]indol-4-yl][2-(cyclohexylamino)ethyl]amine.

25. A compound according to claim 1, which is [9-(2,4-dimethylphenyl)-2-methylpyridino[2,3-b]indol-4-yl][2-(cyclohexylamino)ethyl]amine.

26. A compound according to claim 1, which is [9-(3,5-dimethylphenyl)-2-methylpyridino[2,3-b]indol-4-yl][2-(cyclopentylamino)ethyl]amine.

27. A compound according to claim 1, which is [9-(2,4-dimethylphenyl)-2-methylpyridino[2,3-b]indol-4-yl][2-(cyclopentylamino)ethyl]amine.

28. A compound according to claim 1, which is cyclopentylmethyl(2-{[2-methyl-9-(2,4,6-trimethylphenyl)pyridino[2,3-b]indol-4-yl]amino}ethyl)amine.

29. A method of treating feeding disorders, obesity, bulimia nervosa or hypertension in a mammal which comprises administering to a mammal in need of such treatment a therapeutically effective amount of a compound according to claim 1, a prodrug, or a pharmaceutically acceptable salt thereof.

30. A pharmaceutical composition comprising together with at least one pharmaceutically acceptable carrier.

31. A compound of the formula:

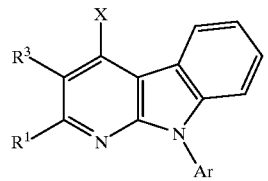

or a pharmaceutically acceptable salt thereof wherein:

Ar is phenyl, 1- or 2-naphthyl, 2-, 3-, or 4-pyridyl, 2-, 4- or 5-pyrimidinyl, each of which is optionally mono-, di-, or trisubstituted with halogen, trifluoromethyl, hydroxy, amino, $C_1$–$C_6$ alkylamino, $C_1$–$C_6$ dialkylamino, $C_3$–$C_7$ cycloalkylamino, carboxamido, $C_1$–$C_6$ alkylcarboxamido, $C_3$–$C_7$ cycloalkylcarboxamido, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, ($C_3$–$C_7$ cycloalkyl) $C_1$–$C_6$ alkoxy, $C_3$–$C_7$ cycloalkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, ($C_3$–$C_7$ cycloalkyl) $C_1$–$C_6$ alkyl, $C_3$–$C_7$ cycloalkyl, or ($C_1$–$C_6$ alkylene)—$G^1$—$R^2$ wherein $G^1$ is oxygen or sulfur and $R^2$ is hydrogen, $C_1$–$C_6$ alkyl, or $C_3$–$C_7$ cycloalkyl;

$R^3$ is hydrogen or $C_1$–$C_6$ alkyl;

X is

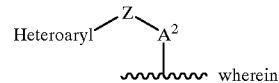

wherein heteroaryl is 1-, 2- or 4-imidazolyl, 2-, 4-, or 5-oxazolyl, 1-, 3-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or di- substituted with halogen, trifluoromethyl, amino, $C_1$–$C_6$ alkylamino, $C_1$–$C_6$ dialkylamino, $C_3$–$C_7$ cycloalkylamino, $C_1$–$C_6$ alkyl, ($C_3$–$C_7$ cycloalkyl) $C_1$–$C_6$ alkyl, $C_3$–$C_7$ cycloalkyl, $C_1$–$C_6$ alkoxy, or $C_3$–$C_7$ cycloalkoxy, with the proviso that tetrazolyl may have at most one substituent; Z is $C_1$–$C_6$ alkylene; and $A^2$ is NH, $SO_2$, oxygen or sulfur.

32. A compound according to claim 31 wherein $R^3$ is hydrogen, $A^2$ is NH or O, and $R^1$ is $C_1$–$C_6$ alkyl.

33. A compound according to claim 32 wherein Ar is 2,4,6-trimethylphenyl, and $A^2$ is NH or O.

34. A compound according to claim 31 wherein $R^3$ is hydrogen, Ar is 2,4,6-trimethylphenyl, and $A^2$ is NH or O.

* * * * *